United States Patent [19]

Müller et al.

[11] Patent Number: 4,940,481
[45] Date of Patent: Jul. 10, 1990

[54] MICROBICIDAL AND GROWTH REGULATING COMPOSITIONS

[75] Inventors: Urs Müller, Münchenstein; Hans Tobler, Allschwil; Hermann Rempfler, Ettingen; Alfred Meyer, Basel, all of Switzerland

[73] Assignee: Ciba-Geigy Corporation, Ardsley, N.Y.

[21] Appl. No.: 468,522

[22] Filed: Feb. 22, 1983

[30] Foreign Application Priority Data

Mar. 4, 1982 [CH] Switzerland ............... 1329/82-5
Nov. 24, 1982 [CH] Switzerland ............... 6850/82-8

[51] Int. Cl.⁵ .............. C07D 249/08; A01N 43/653
[52] U.S. Cl. .................................... 71/76; 71/92; 548/267.4; 548/267.6; 548/268.6
[58] Field of Search ............ 548/101, 262, 341, 336; 424/245, 269, 273 R; 71/76, 77, 78, 92

[56] References Cited

FOREIGN PATENT DOCUMENTS 0040345 11/1981 European Pat. Off. .
0055833 7/1982 European Pat. Off. ............ 424/269
0061835 10/1982 European Pat. Off. ............ 424/269

*Primary Examiner*—Glennon H. Hollrah
*Assistant Examiner*—Patricia L. Morris
*Attorney, Agent, or Firm*—Bruce M. Collins; Edward McC. Roberts

[57] ABSTRACT

The invention relates to azolylpropane derivatives of the general formula I

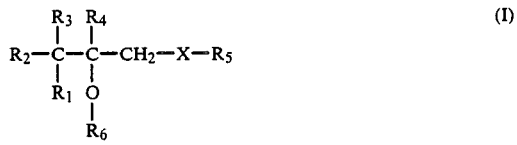

wherein $R_1$ is an azolyl group, $R_2$ and $R_3$, each independently of the other, is hydrogen, alkyl, alkenyl, alkynyl, aralkyl, cyanoalkyl or alkoxycarbonylalkyl, and one of $R_2$ and $R_3$ always has a meaning other than hydrogen, $R_4$ is $C_3$-$C_8$cycloalkyl, unsubstituted or substituted by alkyl; unsubstituted or substituted phenyl; or is $C_1$-$C_{10}$alkyl, unsubstituted or substituted by phenyl or substituted phenyl, $R_5$ is an unsubstituted or a mono- or polysubstituted radical selected from the group consisting of $C_1$-$C_8$alky, $C_3$-$C_8$cycloalkyl, $C_3$-$C_6$alkenyl, $C_3$-$C_6$alkynyl, phenyl, naphthyl, biphenyl, benzylphenyl, benzyloxyphenyl, phenoxyphenyl and aralkyl, $R_6$ is hydrogen, alkyl or alkyl substituted by cyano, alkoxy or alkoxycarbonyl, or is an unsubstituted or substituted radical selected from the group consisting of alkylcarbonyl, phenylcarbonyl, carbamoyl, aralkyl, alkoxycarbonyl, alkylsulfonyl, phenylsulfonyl or sulfamoyl, and X is oxygen or sulfur, including the acid addition salts, quaternary azolium salts and metal complexes thereof.

The invention further discloses methods of preparing these compounds as well as agrochemical compositions which contain one of said compounds as active component. The invention relates further to a method of controlling phytopathogenic microorganisms and/or of regulating plant growth with the compounds of formula I.

6 Claims, No Drawings

MICROBICIDAL AND GROWTH REGULATING COMPOSITIONS

The present invention relates to novel substituted azolylpropane derivatives and to the acid addition salts, quaternary azolium salts and metal complexes thereof. The invention relates further to the preparation of these compounds and to microbicidal and growth regulating compositions which contain at least one of these compounds. The invention relates also to the preparation of said compositions and to the use of the novel compounds or compositions for regulating plant growth and for controlling harmful microorganisms. The invention relates in addition to azolylmethyloxiranes prepared as intermediates.

The azolylpropane derivatives of the present invention have the general formula I

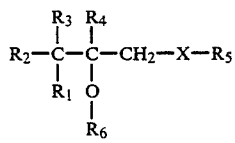

wherein
  $R_1$ is an azolyl group,
  $R_2$ and $R_3$, each independently of the other, is hydrogen, alkyl, alkenyl, alkynyl, aralkyl, cyanoalkyl or alkoxycarbonylalkyl, and one of $R_2$ and $R_3$ always has a meaning other than hydrogen,
  $R_4$ is $C_3$–$C_8$cycloalkyl, unsubstituted or substituted by alkyl; unsubstituted or substituted phenyl; or is $C_1$–$C_{10}$alkyl, unsubstituted or substituted by phenyl or substituted phenyl,
  $R_5$ is an unsubstituted or a mono- or polysubstituted radical selected from the group consisting of $C_1$–$C_8$alkyl, $C_3$–$C_8$cycloalkyl, $C_3$–$C_6$alkyl, $C_3$–$C_6$alkynyl, phenyl, naphthyl, biphenyl, benzylphenyl, benzyloxyphenyl, phenoxyphenyl and aralkyl,
  $R_6$ is hydrogen, alkyl or alkyl substituted by cyano, alkoxy or alkoxycarbonyl, or is an unsubstituted or substituted radical selected from the group consisting of alkylcarbonyl, phenylcarbonyl, carbamoyl, aralkyl, alkoxycarbonyl, alkylsulfonyl, phenylsulfonyl or sulfamoyl, and
  X is oxygen or sulfur,
including the acid addition salts, quaternary azolium salts and metal complexes thereof.

The term azolyl denotes a 5-membered heterocyclic ring containing nitrogen as heteroatom and having aromatic character. Typical representatives are 1H-1,2,4-triazole, 4H-1,2,4-triazole and 1H-imidazole. Depending on the indicated number of carbon atoms, alkyl by itself or as moiety of another substituent such as alkoxy, alkylthio, haloalkyl, haloalkylthio, aralkyl, alkylcarbonyl, alkylsulfonyl or alkylimino, comprises e.g. the following groups: methyl, ethyl, propyl, butyl, pentyl, hexyl, heptyl, octyl, nonyl or decyl, and the isomers thereof, e.g. isopropyl, isobutyl, sec-butyl, tert-butyl, isopentyl etc. Haloalkyl is a trihalogenated to perhalogenated alkyl substituent, e.g. $CHCl_2$, $CF_3$, $CHF_2$, $CH_2Cl$, $CCl_3$, $CH_2F$, $CH_2CH_2Cl$, $CHBr_2$, etc. Throughout this specification, halogen denotes fluorine, chlorine, bromine or iodine, with fluorine, chlorine or bromine being preferred. Naphthyl is α- or β-naphthyl, with α-naphthyl being preferred. Alkenyl is e.g. propen-1-yl, allyl, buten-1-yl, buten-2-yl or buten-3-yl. Alkynyl is e.g. propion-1-yl or propargyl. Aryl is e.g. naphthyl, especially phenyl; and aralkyl is a lower alkyl radical which is substituted by an aromatic group, e.g. benzyl or phenylethyl. Depending on the indicated number of carbon atoms, cycloalkyl is e.g. cyclopropyl, cyclobutyl, cyclopentyl, cyclohexyl, cycloheptyl, cyclooctyl etc.

Accordingly, the present invention relates to the free compounds of the formula I and to the acid addition salts, quaternary azolium salts and metal complexes thereof. The free compounds are preferred.

Examples of salt-forming acids are inorganic acids, e.g. hydrohalic acids such as hydrofluoric acid, hydrochloric acid, hydrobromic acid or hydriodic acid, and also sulfuric acid, phosphoric acid, phosphorous acid, nitric acid; and organic acids such as acetic acid, trifluoroacetic acid, trichloroacetic acid, propionic acid, glycolic acid, thiocyanic acid, lactic acid, succinic acid, citric acid, benzoic acid, cinnamic acid, oxalic acid, formic acid, benzenesulfonic acid, p-toluenesulfonic acid, methanesulfonic acid, salicylic acid, p-aminosalicylic acid, 2-phenoxybenzoic acid or 2-acetoxybenzoic acid.

Metal complexes of the formula I consist of the basic organic molecule and an inorganic or organic metal salt, for example the halides, nitrates, sulfates, phosphates, acetates, trifluoroacetates, trichloroacetates, propionates, tartrates, sulfonates, salicylates, benzoates etc. of the elements of the third and fourth main group of the Periodic Table such as aluminium, tin or lead, and of the first to eighth auxiliary group such as chromium, manganese, iron, cobalt, nickel, copper, zinc, silver, mercury etc. Preferred elements are those of the auxiliary groups of the fourth period. The metals may exist in different valency states. The metal complexes of the formula I may be mononuclear or polynuclear, i.e. they can contain one or more parts of the organic molecule as ligands. Complexes with copper, zinc, manganese and tin are preferred.

1-Hydroxyethylazole derivatives as growth regulators and fungicides are known from the literature, e.g. from European patent application 40 345.

The compounds of formula I are oils, resins or mainly solids which are stable at room temperature and have very valuable microbicidal and growth regulating properties. They can be used in agriculture or related fields preventively and curatively for controlling phytopathological microorganisms and for regulating plant growth, for which utility the triazolylmethyl derivatives falling within the scope of formula I are preferred. The compounds of formula I are very well tolerated by cultivated plants.

On account of their pronounced growth regulating and/or microbicidal properties, those compounds are preferred in which:
  (a) the azolyl group $R_1$ is 1H-1,2,4-triazole, 4H-1,2,4-triazole or 1H-imidazole, or
  (b) each of $R_2$ and $R_3$ independently of the other is $C_1$–$C_6$alkyl, $C_3$–$C_6$alkenyl, $C_3$–$C_6$alkynyl, cyanoalkyl containing 1 to 4 carbon atoms in the alkyl moiety, aralkyl containing 1 to 4 carbon atoms in the alkyl moiety and, in the aryl moiety, a phenyl ring which is unsubstituted or substituted by a member selected from halogen, $C_1$–$C_4$alkyl, cyano, $C_1$–$C_4$alkoxy, $C_1$–$C_4$haloalkoxy, $C_1$–$C_4$haloalkyl, $C_1$–$C_4$alkylthio, $C_1$–$C_4$haloalkylthio or nitro, or is alkoxycarbonylalkyl containing not more than 4 carbon atoms in the respective alkoxy and alkyl moiety; or (c) $R_4$ is $C_3$-$C_8$cycloalkyl substituted by $C_1$-$C_4$alkyl; $C_1$-$C_{10}$alkyl which is unsubstituted or substituted by phenyl or substituted phenyl, or is unsubstituted or substituted phenyl, the substituents of the phenyl nucleus being selected from the group consisting of halogen, cyano, nitro, $C_1$-$C_4$alkyl, $C_1$-$C_4$alkoxy, $C_1$-$C_4$alkylthio, $C_1$-$C_4$haloalkyl, $C_1$-$C_3$haloalkoxy or $C_1$-$C_4$haloalkylthio; or (d) the substituents of the radicals represented by $R_5$ are selected from the group consisting of halogen, cyano, nitro, $C_1$-$C_4$alkyl, $C_1$-$C_4$alkoxy, $C_1$-$C_4$alkylthio, $C_1$-$C_4$haloalkyl, $C_1$-$C_4$haloalkoxy or $C_1$-$C_4$haloalkylthio; or (e) $R_6$ is hydrogen, $C_1$-$C_6$alkyl which is unsubstituted or substituted by cyano, $C_1$-$C_4$alkoxy or $C_1$-$C_4$alkoxycarbonyl, or is $C_1$-$C_6$alkylcarbonyl which is unsubstituted or substituted in the alkyl moiety by cyano, $C_1$-$C_4$alkoxycarbonyl, $C_1$-$C_4$alkoxy or dialkylamino containing not more than 6 carbon atoms; or is phenylcarbonyl which is unsubstituted or substituted in the phenyl moiety by halogen, $C_1$-$C_4$alkyl, $C_1$-$C_4$haloalkyl or $C_1$-$C_4$alkoxy, or is carbamoyl in which hydrogen, $C_1$-$C_4$alkoxy or $C_1$-$C_4$alkyl, each independently of the other, are attached to the nitrogen atom or in which the nitrogen atom is a member of a 5- or 6-membered saturated heterocyclic ring which may contain an oxygen atom or a $C_1$-$C_4$alkylimino group as additional ring member, or is benzyl or benzyl which is substituted by 1 to 3 halogen atoms or 1 to 3 $C_1$-$C_4$alkoxy or $C_1$-$C_4$alkyl groups, or is $C_1$-$C_4$alkoxycarbonyl or $C_1$-$C_4$alkylsulfonyl, or is phenylsulfonyl which is unsubstituted or substituted by halogen or $C_1$-$C_4$alkyl, or is sulfamoyl in which hydrogen or $C_1$-$C_4$alkyl, each independently of the other, are attached to the nitrogen atom or in which the nitrogen atom is a member of a 5- or 6-membered saturated heterocyclic ring system which may contain an oxygen atom or a $C_1$-$C_4$alkylimino group as additional ring member.

Preferred compounds of groups (a) to (e) above are those in which (aa) $R_1$ is 1H-1,2,4-triazol-1-yl, or (bb) $R_2$ and $R_3$, each independently of the other, are hydrogen, $C_1$-$C_4$alkyl, benzyl or benzyl substituted by halogen; or (cc) $R_4$ is $C_1$-$C_6$alkyl, phenyl or phenyl substituted by a member selected from the group consisting of halogen, cyano, nitro, $C_1$-$C_4$alkyl, $C_1$-$C_4$alkoxy, $C_1$-$C_4$alkylthio, $C_1$-$C_4$haloalkyl, $C_1$-$C_4$haloalkoxy or $C_1$-$C_4$haloalkylthio, and is preferably tert-butyl; or (dd) $R_5$ is $C_1$-$C_8$alkyl, $C_3$-$C_8$cycloalkyl, phenylalkyl containing 1 to 4 carbon atoms in the alkyl moiety, or is phenyl or phenyl substituted by a member selected from the group consisting of halogen, cyano, nitro, $C_1$-$C_4$alkyl, $C_1$-$C_4$alkoxy, $C_1$-$C_4$alkylthio, $C_1$-$C_4$haloalkyl, $C_1$-$C_4$haloalkoxy or $C_1$-$C_4$haloalkylthio; or (ee) $R_6$ is hydrogen, $C_1$-$C_4$alkyl, phenylalkyl containing 1 to 4 carbon atoms in the alkyl moiety, $C_1$-$C_6$alkylcarbonyl, carbamoyl containing not more than 3 carbon atoms, $C_1$-$C_4$alkoxycarbonyl, $C_1$-$C_4$alkylsulfonyl, phenylsulfonyl which is unsubstituted or substituted by $C_1$-$C_4$alkyl, or is sulfamoyl containing not more than 2 carbon atoms, with compounds in which $R_6$ is hydrogen, methyl, benzyl, acetyl, methylcarbamoyl, N,N-dimethylcarbamoyl, N-methoxy-N-methylcarbamoyl, methoxycarbonyl, ethoxycarbonyl, methylsulfonyl, 4-tolylsulfonyl, methylsulfamoyl or N,N-dimethylsulfamoyl constituting a preferred subgroup.

Particularly preferred groups of compounds result from a combination of a number of subgroups. These groups comprise compounds in which:

$R_1$ is 1H-1,2,4-triazole, 4H-1,2,4-triazole or 1H-imidazole, $R_2$ and $R_3$, each independently of the other, are hydrogen, $C_1$-$C_4$alkyl, $C_3$-$C_6$alkenyl, $C_3$-$C_6$alkynyl, cyanoalkyl containing 1 to 4 carbon atoms in the alkyl moiety, aralkyl containing 1 to 4 carbon atoms in the alkyl moiety and, in the aryl moiety, a phenyl ring which is unsubstituted or substituted by a member selected from the group consisting of halogen, $C_1$-$C_4$alkyl, cyano, $C_1$-$C_4$alkoxy, $C_1$-$C_4$haloalkoxy, $C_1$-$C_4$haloalkyl, $C_1$-$C_4$alkylthio, $C_1$-$C_4$haloalkylthio or nitro, or are alkoxycarbonylalkyl containing not more than 4 carbon atoms in the respective alkoxy and alkyl moiety;

$R_4$ is $C_3$-$C_8$cycloalkyl substituted by $C_1$-$C_4$alkyl; $C_1$-$C_{10}$alkyl which is unsubstituted or substituted by phenyl or substituted phenyl, or is unsubstituted or substituted phenyl, the substituents of the phenyl nucleus being selected from the group consisting of halogen, cyano, nitro, $C_1$-$C_4$alkyl, $C_1$-$C_4$alkoxy, $C_1$-$C_4$alkylthio, $C_1$-$C_4$haloalkyl, $C_1$-$C_4$haloalkoxy or $C_1$-$C_4$haloalkylthio;

the substituents of the radicals represented by $R_5$ are selected from the group consisting of halogen, cyano, nitro, $C_1$-$C_4$alkyl, $C_1$-$C_4$alkoxy, $C_1$-$C_4$alkylthio, $C_1$-$C_4$haloalkyl, $C_1$-$C_4$haloalkoxy or $C_1$-$C_4$haloalkylthio; and $R_6$ is hydrogen, $C_1$-$C_6$alkyl which is unsubstituted or substituted by cyano, $C_1$-$C_4$alkoxy or $C_1$-$C_4$alkoxycarbonyl, or is $C_1$-$C_6$alkylcarbonyl which is unsubstituted or substituted in the alkyl moiety by cyano, $C_1$-$C_4$alkoxycarbonyl, $C_1$-$C_4$alkoxy or dialkylamino containing not more than 6 carbon atoms, or is phenylcarbonyl which is unsubstituted or substituted in the phenyl moiety by halogen, $C_1$-$C_4$alkyl, $C_1$-$C_4$haloalkyl or $C_1$-$C_4$alkoxy, or is carbamoyl in which hydrogen, $C_1$-$C_4$alkoxy or $C_1$-$C_4$alkyl, each independently of the other, are attached to the nitrogen atom or in which the nitrogen atom is a member of a 5- or 6-membered saturated heterocyclic ring which may contain an oxygen atom or a $C_1$-$C_4$alkylimino group as additional ring member, or is $C_1$-$C_4$alkoxycarbonyl or $C_1$-$C_4$alkylsulfonyl, or is phenylsulfonyl which is unsubstituted or substituted by halogen or $C_1$-$C_4$alkyl, or is sulfamoyl in which hydrogen or $C_1$-$C_4$alkyl, each independently of the other, are attached to the nitrogen atom or in which the nitrogen atom is a member of a 5- or 6-membered saturated heterocyclic ring system which may contain an oxygen atom or a $C_1$-$C_4$alkylimino group as additional ring member; or in which $R_1$ is 1H-1,2,4-triazol-1-yl, $R_2$ and $R_3$, each independently of the other, are hydrogen or $C_1$-$C_4$alkyl, $R_4$ is $C_1$-$C_6$alkyl, phenyl or phenyl substituted by a member selected from the group consisting of halogen, cyano, nitro, $C_1$-$C_4$alkyl, $C_1$-$C_4$alkoxy, $C_1$-$C_4$alkylthio, $C_1$-$C_4$haloalkyl, $C_1$-$C_4$haloalkoxy or $C_1$-$C_4$haloalkylthio, $R_5$ is $C_1$-$C_8$alkyl, $C_3$-$C_8$cycloalkyl, phenylalkyl containing 1 to 4 carbon atoms in the alkyl moiety, or is phenyl or phenyl substituted by a member selected from the group consisting of halogen, cyano, nitro, $C_1$-$C_4$alkyl, $C_1$-$C_4$alkoxy, $C_1$-$C_4$alkylthio, $C_1$-$C_4$haloalkyl, $C_1$-$C_4$haloalkoxy or $C_1$-$C_4$haloalkylthio; and $R_6$ is hydrogen, methyl, benzyl, acetyl, methylcarbamoyl, N,N-dimethylcarbamoyl, N-methoxy-N-methylcarbamoyl, methoxycarbonyl, ethoxycarbonyl, methylsulfonyl, 4-tolylsulfonyl, methylsulfamoyl or N,N-dimethylsulfamoyl.

A particularly preferred subgroup comprises those compounds of the formula I, wherein $R_1$ is 1H-1,2,4-triazol-1-yl, $R_2$ is methyl or ethyl, $R_3$ is hydrogen, $R_4$ is isopropyl or tert-butyl, $R_5$ is phenyl or phenyl substituted by 1 or 2 methyl or nitro groups or 1 or 2 fluorine, chlorine or bromine atoms, X is oxygen and $R_6$ is hydrogen or methyl.

The following individual compounds are preferred:
1-(4-chlorophenoxy)-2-tert-butyl-2-hydroxy-3-methyl-3-(1H-1,2,4-triazol-1-yl)-propane,
1-(4-fluorophenoxy)-2-tert-butyl-2-hydroxy-3-methyl-3-(1H,-1,2,4-triazol-1-yl)-propane,
1-phenoxy-2-tert-butyl-2-methoxy-3-methyl-3-(1H-1,2,4-triazol-1-yl)-propane,
1-phenoxy-2-tert-butyl-2-hydroxy-3-ethyl-3-(1H-1,2,4-triazol-1-yl)-propane,
1-(4-toluyloxy)-2-tert-butyl-2-hydroxy-3-methyl-3-(1H-1,2,4-triazol-1-yl)-propane,
1-(4-fluorophenoxy)-2-tert-butyl-2-hydroxy-3-ethyl-3-(1H-1,2,4-triazol-1-yl)-propane,
1-(2-fluorophenoxy)-2-tert-butyl-2-hydroxy-3-methyl-3-(1H-1,2,4-triazol-1-yl)-propane,
1-(4-nitrophenoxy)-2-tert-butyl-2-hydroxy-3-methyl-3-(1H-1,2,4-triazol-1-yl)-propane,
1-(2,3-dimethylphenoxy)-2-tert-butyl-2-hydroxy-3-methyl-3-(1H-1,2,4-triazol-1-yl)-propane,
1-(4-chloro-2-methylphenoxy)-2-tert-butyl-2-hydroxy-3-methyl-3-(1H-1,2,4-triazol-yl)-propane,
1-(4-bromophenoxy)-2-isopropyl-2-hydroxy-3-methyl-3-(1H-1,2,4-triazol-1-yl)-propane,
1-(4-fluorophenoxy)-2-isopropyl-2-hydroxy-3-methyl-3-(1H-1,2,4-triazol-1-yl)-propane and
1-(4-bromophenoxy)-2-tert-butyl-2-hydroxy-3-methyl-3-(1H-1,2,4-triazol-1-yl)-propane.

The compounds of the formula I are obtained by reacting an azolylmethyloxirane of the formula II

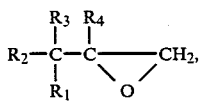

wherein $R_1$, $R_2$, $R_3$ and $R_4$ are as defined for formula I, with an alcohol or thioalcohol of the formula III

wherein X and $R_5$ are as defined for formula I, in the presence of a base and in an inert solvent, and, if desired, etherifying or esterifying the resultant compound of the formula Ia

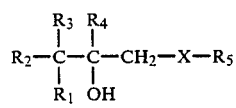

by reaction with an etherifying or esterifying agent of the formula IV

wherein $R_6$ is as defined for formula I and Y is a halogen atom or the radical of an organic or inorganic acid.

The reaction of the compound of formula II with the compound of formula III is conveniently carried out in the presence of a catalytic amount of a base as condensing agent. Examples of suitable bases are organic and inorganic bases, e.g. tertiary amines such as trialkylamines (trimethylamine, triethylamine, tripropylamine etc.), pyridine and pyridine bases (4-dimethylaminopyridine, 4-pyrrolidylaminopyridine etc), oxides, hydrides and hydroxides, carbonates and bicarbonates of alkali metals and alkaline earth metals (CaO, BaO, NaOH, LiOH, $CaH_2$, KOH, NaH, $Ca(OH)_2$, $KHCO_3$, $NaHCO_3$, $Ca(HCO_3)$, $K_2CO_3$, $Na_2CO_3$), as well as alkali alcoholates such as $CH_3COONa$ or $CH_3COOK$. Also suitable are alkali alcoholates such as $C_2H_5ONa$, $C_3H_7$—nONa, $(CH_3)_3C$—OK etc.

The reaction of the compound of formula (II) with the compound of formula (III) is preferably conducted in a relatively polar but inert organic solvent, e.g. N,N-dimethylformamide, N,N-dimethylacetamide, dimethylsulfoxide, acetonitrile, benzonitrile, ethylene glycol dimethyl ether, diethylene glycol dimethyl ether, triethylene glycol dimethyl ether, dioxan, tetrahydrofuran and the like. However, such reactions may also be conducted in combination with other inert solvents, e.g. benzene, toluene, xylene, hexane, petroleum ether, chlorobenzene, nitrobenzene and the like. The reaction temperature is in the range from 20° to 250° C., preferably from 80° to 180° C.

The optional reaction of the compound of the subformula Ia to give the compound of the formula I, in which $R_6$ has a meaning different from hydrogen, is conveniently carried out in an inert organic solvent. Suitable solvents are aprotic solvents such as N,N-dimethylformamide, N,N-dimethylacetamide, dimethylsulfoxide, acetonitrile, benzonitrile, N-methylpyrrolidone, N-methylpiperidinone, benzene, toluene, xylene, hexane, cyclohexane, chlorobenzene, nitrobenzene and the like.

If the —O—$R_6$ group is an ether group, Y will normally be halogen such as chlorine, bromine or iodine, or is an acid radical which is derived from a strong acid, e.g. sulfuric acid, phosphoric acid, a sulfonic acid, preferably a haloalkylsulfonic acid, or from a haloalkanecarboxylic acid such as trifluoroacetic acid. Typical representatives of such acid derivatives are dimethyl sulfate, diethyl sulfate and methyl trifluoromethanesulfonate. If the —O—$R_6$ group is an ester group, Y will normally be halogen such as chlorine or bromine, or an acid radical of an acid which is able to form an anhydride with the transferred acyl radical. Such anhydrides are preferably anhydrides with the same acid. Accordingly, the reagent Y—$R_6$ may be acetic anhydride, propionic anhydride, benzoic anhydride, benzenesulfonic anhydride or trifluorosulfonic anhydride.

The etherification or esterification of the compounds of the subformula Ia is conveniently carried out in the presence of a base such as an alcoholate, hydroxide, hydride, carbonate or bicarbonate of an alkali metal or alkaline earth metal. The reaction temperature is in the range from 20° to 150° C., preferably from 60° to 120° C.

The compounds of the formula I are obtained in the form of mixtures of diastereoisomers. The invention relates to all diastereoisomers of the compounds of formula I and mixtures thereof. Accordingly, both the pure diastereoisomers and the individual optical isomers of the pairs of enantiomers fall within the province of the invention.

The alcohols or thioalcohols of the formula III as well as etherifying and esterifying agents of the formula IV are known or can be prepared by methods which are known per se.

The oxiranes of the formula II are novel and constitute intermediates which have been especially developed for the preparation of the valuable compounds of the formula I. On account of their structure they can be readily converted into the compounds of formula I.

Like the final products of the formula I, the oxiranes of the formula II have growth regulating and microbicidal properties. They can therefore be employed as active ingredients in corresponding agrochemical compositions. Such compositions also constitute a further object of the invention.

The oxiranes of the formula II can be prepared by reacting the ketone of the formula V

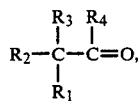

wherein $R_1$, $R_2$, $R_3$ and $R_4$ are as defined for formula I, with dimethylsulfonium methylide, dimethyloxosulfonium methylide or the corresponding salts such as trimethylsulfonium iodide or trimethyloxosulfonium iodide, in the presence of a strong base such as an alkali metal alcoholate or alkaline earth metal alcoholate, an alkali metal hydroxide or an alkali metal hydride or alkaline earth metal hydride, in dimethylsulfoxide or in one of the other solvents specified for the reaction of the compound of formula II with the compound of the formula III. In appropriate circumstances, the preparation of the sulfonium ylide and the reaction of the sulfonium salt with the base may also be carried out by the phase transfer process. Suitable phase transfer catalysts are quaternary ammonium salts such as trialkylphenylalkylammonium salts or tetraalkylammonium salts, quaternary phosphonium salt such as tetraalkylphosphonium salts, or crown ethers such as 15-crown-5 or 18-crown-6. In this reaction, the sulfonium ylide is prepared in situ and reacted direct with the ketone of the formula V to give the oxirane of the formula II. The reaction is carried out in the temperature range from 0° to 120° C.

Corresponding reactions are known from the literature [q.v. JACS 87, 1353 (1965)]. In principal, the reaction can be carried out in similar manner to the reactions described therein.

Ketones of the formula V can be obtained from the known α-haloketones of the formula VI

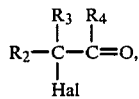

wherein $R_2$, $R_3$ and $R_4$ are as defined for formula I and Hal is chlorine or bromine, by reaction with azoles of the formula VII

 (VII)

wherein $R_1$ is as defined for formula I, in the presence of a base.

The ketones of the formula V can also be obtained by reacting an azolylmethyl ketone of the formula VIII

with compounds of the formula IX and/or X

or

wherein $R_2$ and $R_3$ are as defined for formula I and Z is a halogen atom or the radical of an organic or inorganic acid, in the presence of a base.

The preparation of the ketones of the formula V is carried out in conventional solvents and optionally at elevated temperature.

The compounds of the formulae VI, VII, VIII, IX and X are known, and some are commercially available, or they can be prepared by known methods.

Unless otherwise expressly specified, one or more inert solvents or diluents may be present in the preparation of all starting materials, intermediates and final products mentioned herein. Examples of suitable inert solvents or diluents are: aliphatic and aromatic hydrocarbons such as benzene, toluene, xylenes, petroleum, ether, halogenated hydrocarbons such as chlorobenzene, methylene chloride, ethylene chloride, chloroform; carbon tetrachloride, tetrachloroethylene; ethers and ethereal compounds such as dialkyl ethers (diethyl ether, diisopropyl ether, tert-butylmethyl ether etc.), anisole, dioxane, tetrahydrofuran; nitriles such as acetonitrile, propionitrile; N,N-dialkylated amides such as dimethylformamide; dimethylsulfoxide; ketones such as acetone, diethyl ketone, methyl ethyl ketone; and mixtures of such solvents with each other. It can often be convenient to carry out the reaction, or partial steps of a reaction, under an inert gas atmosphere and/or in absolute solvents. Suitable inert gases are nitrogen, helium, argon or, in certain cases, also carbon dioxide.

The process for obtaining the compounds of formula I, including all partial steps, constitutes an important object of the present invention.

Surprisingly, it has now been found that the novel compounds of the formula I and compositions containing them are characterised in particular by their selective influence on plant metabolism. This selective influence on the physiological processes of plant development makes it possible to use the compounds of formula I for different purposes, especially for those in connection with increasing the yield of useful plants, with facilitating harvesting, and with labour-saving in measures taken in crops of cultivated plants.

Previous experience with the application of growth regulators has show that the active ingredients can induce one or more different responses in the plants. These different responses depend largely on the time of application, based on the development state of the seed or plant, as well as on the concentrations of active ingredient applied to the plants or the locus thereof. Growth regulators should at all events induce positive responses in the cultivated plants in the desired manner.

Growth regulators may be used e.g. for inhibiting vegetative plant growth. Such a growth inhibition is of economic interest, inter alia, in respect of grasses, as the frequency of cutting in flower gardens, parks, sports fields or road shoulders can thereby be reduced. Of importance too is the inhibition of growth of herbaceous and ligneous plants on road shoulders and near transmission lines, or generally in areas in which strong growth is undesirable.

The use of growth regulators for inhibiting the growth in height of cereals is also important, as shortening the stalks diminishes or completely eliminates the danger of lodging before harvesting. In addition, growth regulators are able to bring about a strengthening of the stalks in crops of cereals and this too counteracts lodging.

Inhibition of the vegetative growth of many cultivated plants permits more plants to be sown in a crop area, so that a higher yield may be obtained per unit of area. A further mechanism of yield increase using growth regulators resides in the fact that nutrients are able increasingly to promote flower formation and fruiting, whilst vegetative growth is inhibited.

Growth regulators are also frequently able to promote vegetative growth. This is of great value when the vegetative parts of plants are to be harvested. However, promotion of vegetative growth can also result simultaneously in promotion of generative growth, so that e.g. more or larger fruit is formed.

Yield increases may also often be obtained by influencing the plant metabolism without any visible changes in vegetative growth. Growth regulators can also induce a change in the composition of plants, so that the quality of the harvest produce is improved. For example, it is possible to increase the sugar content of sugar beet, sugar cane, pineapples and citrus fruit, or to increase the protein content of soya beans or cereals.

The use of growth regulators can lead to the formation of parthenocarpic fruit. The sex of blossoms can also be influenced. The production or flow of secondary plant substances can also be positively influenced by growth regulators, for example the stimulation of the flow of latex in rubber trees.

During plant growth, the development of side-shoots can also be promoted by the chemical interruption of apical dominance using growth regulators. This is of interest e.g. in the propagation of plant cuttings. However, it is also possible to inhibit the growth of side-shoots, e.g. in tobacco plants after decapitation in order to prevent the formation of side-shoots and thus to promote leaf growth.

Premature fruit drop can be prevented by the use of growth regulators. However, it is also possible to promote fruit drop—e.g. in fruit crops—by means of chemical thinning up to a specific degree. Growth regulators can also be used for reducing the force necessary for detaching fruit at harvesting, thus making possible mechanical harvesting of plants or facilitating manual harvesting.

With growth regulators it is also possible to speed up or delay the ripening of harvest products before or after harvesting. This is particularly advantageous, because a best possible accomodation to market requirements can thereby be achieved. In addition, growth regulators can often improve the colour of fruit. With the aid of growth regulators it is also possible to concentrate ripening at a particular time. The conditions are thus created for a complete mechanical harvesting of e.g. tobacco, tomatoes or coffee, or for manual harvesting, in only one single operation.

The application of growth regulators can also make it possible to influence the dormancy of seeds and buds of plants, i.e. the endogenic annual rhythm, so that plants such as pineapples or ornamentals in nurseries germinate, sprout or blossom at a time when they would normally not tend to do so.

With growth regulators it is also possible to delay budding or the germination of seeds, e.g. in order to avoid damage by late frosts in areas endangered thereby. Conversely, root growth and/or the formation of shoots can be stimulated, so that growth may be restricted to a shorter period.

Growth regulators can also impart halophilic properties to cultivated plants. The conditions are thus created for cultivating plants in salty soil. Growth resulators can also impart to plants resistance to frost and drought.

Under the influence of growth regulators, the ageing (senescence) of plants or parts of plants can be inhibited or delayed. Such an action can be of great economic importance, as the storability of treated parts of plants or whole plants such as fruit, berries, vegetables, salads or ornamentals can be improved or prolonged after harvesting. Likewise, a substantial yield increase can be obtained by treating cultivated plants by prolonging the phase of photosynthetic activity.

A further important field of use for growth regulators is the inhibition of excessive growth of tropical cover crops. In tropical and subtropical monocultures, e.g. in palm tree plantations, cotton and maize fields etc., cover crops, especially species of leguminosae, are often planted with the object of maintaining or improving the quality of the soil (prevention of desiccation, supplying nitrogen) and for preventing erosion. By applying the compounds of this invention it is possible to control the growth of these cover crops and so to keep the growth in height of these plants at a low level, thus ensuring healthy growth of the cultivated plants and the maintenance of favourable soil conditions.

Surprisingly, it has also been found that, in addition to their advantageous growth regulating properties, the compounds of formula I and the compositions containing them also have for practical purposes a very useful microbicidal spectrum. A further field of use of the compounds of formula I is therefore the control of harmful microorganisms, especially phytopathogenic fungi. The compounds of formula thus have for practical purposes a very useful curative, preventive and systemic action for protecting plants, especially cultivated plants, without adversely affecting them. With the compounds of formula I it is possible to inhibit or destroy the microorganisms which occur in plants or parts of plants (fruit, blossoms, leaves, stems, tubers, roots) in different crops of useful plants, while at the same time the parts of plants which grow later are also protected from attack by such microorganisms.

The compounds of formula I are effective against the phytopathogenic fungi belonging to the following classes: Ascomycetes (e.g. Venturia, Podosphaera, Erysiphe, Monilinia, Uncinula); Basidomycetes (e.g. the genera Hemileia, Rhizoctonia, Puccinia); Fungi imperfecti (e.g. Botrytis, Helminthosphorium, Fusarium, Septoria, Cercospora and Alternaria). In addition, the compounds of formula I have a systemic action. They can also be used as seed dressing agents for protecting seeds (fruit, tubers, grains) and plant cuttings against fungus infections as well as against phytopathogenic microorganisms which occur in the soil.

The compounds of the invention are especially well tolerated by plants.

Accordingly, the invention also relates to microbicidal compositions and to the use of compounds of the formula I for controlling phytopathogenic microorganisms, especially harmful fungi, and for the preventive treatment of plants to protect them from attack by such microorganisms.

The invention further relates to the preparation of agrochemical compositions, which comprises homogeneously mixing the active ingredient with one or more compounds or groups of compounds described herein. The invention furthermore rleates to a method of treating plants, which comprises applying thereto the compounds of the formula I or the novel compositions.

Target crops to be protected within the scope of the present invention comprise e.g. the following species of plants: cereals (wheat, barley, rye, oats, rice, sorghum and related crops); beet (sugar beet and fodder beet); drupes, pomes and soft fruit (apples, pears, plums, peaches, almonds, cherries, strawberries, rasberries and blackberries); leguminous plants (beans, lentils, peas, soybeans); oil plants (rape, mustard, poppy, olives, sunflowers, coconuts, castor oil plants, cocoa beans, groundnuts); cucumber plants (cucumber, marrows, melons); fibre plants (cotton, flax, hemp, jute); citrus fruit (oranges, lemons, grapefruit, mandarins); vegetables (spinach, luttuce, asparagus, cabbages, carrots, onions, tomatoes, potatoes, paprika); lauraceae (avocados, cinnamon, camphor); or plants such as maize, tobacco, nuts, coffee, sugar cane, tea, vines, hops, bananas and natural rubber plants, as well as ornamentals (composites), areas of grass, embankments or general low cover crops which counteract erosion or desication of the soil and are useful in cultures of trees and perennials (fruit plantations, hop plantations, maize fields, vineyards etc.).

The compounds of formula I are normally applied in the form of compositions and can be applied to the crop area or plant to be treated, simultaneously or in succession, with further compounds. These compounds can be both fertilisers or micronutrient donors or other preparations that influence plant growth. They can also be selective herbicides, insecticides, fungicides, bactericides, nematicides, mollusicides or mixtures of several of these compositions, if desired together with further carriers, surfactants or application-promoting adjuvants customarily employed in the art of formulation. Suitable carriers and adjuvants can be solid or liquid and correspond to the substances ordinarily employed in formulation technology, e.g. natural or regenerated mineral substances, solvents, dispersants, wetting agents, tackifiers, binders or fertilisers.

A preferred method of applying a compound of the formula I or an agrochemical composition which contains at least one of said compounds, is foliar application. The number of applications and the rate of application depend on the intensity of infestation by the corresponding pathogen (type of fungus) or on the manner in which growth is influenced. However, the compounds of formula I can also penetrate the plant through the roots via the soil (systemic action) by impregnating the locus of the plant with a liquid composition, or by applying the compounds in solid form to the soil, e.g. in granular form (soil application). The compounds of formula I may also be applied to seeds (coating) by impregnating the seeds either with a liquid formulation containing a compound of the formula I, or by coating them with a solid formulation. In special cases, further types of application are also possible, e.g. selective treatment of the plant stems or buds.

The compounds of the formula I are used in unmodified form or, preferably, together with the adjuvants conventionally employed in the art of formulation, and are therefore formulated in known manner to emulsifiable concentrates, coatable pastes, directly sprayable or dilutable solutions, dilute emulsions, wettable powders, soluble powders, dusts, granulates, and also encapsulations in e.g. polymer substances. As with the nature of the compositions, the methods of application, such as spraying, atomising, dusting, scattering or pouring, are chosen in accordance with the intended objectives and the prevailing circumstances. Advantageous rates of application are normally from 10 g to 5 kg of active ingredient (a.i.) per hectare, preferably from 100 g to 2 kg a.i./ha, most preferably from 200 g to 600 g a.i./ha.

The formulations, i.e. the compositions containing the compound (active ingredient) of the formula I and, where appropriate, a solid or liquid adjuvant, are prepared in known manner, e.g. by homogeneously mixing and/or grinding the active ingredients with extenders, e.g. solvents, solid carriers and, where appropriate, surface-active compounds (surfactants).

Suitable solvents are: aromatic hydrocarbons, preferably the fractions containing 8 to 12 carbon atoms, e.g. xylene mixtures or substituted naphthalenes, phthalates such as dibutyl phthalate or dioctyl phthalate, aliphatic hydrocarbons such as cyclohexane or paraffins, alcohols and glycols and their ethers and esters, such as ethanol, ethylene glycol monomethyl or monoethyl ether, ketones such as cyclohexanone, strongly polar solvents such as N-methyl-2-pyrrolidone, dimethylsulfoxide or dimethylformamide, as well as epoxidised vegetable oils such as epoxidised coconut oil or soybean oil; or water.

The solid carriers used e.g. for dusts and dispersible powders, are normally natural mineral fillers such as calcite, talcum, kaolin, montmorillonite or attapulgite. In order to improve the physical properties it is also possible to add highly dispersed silicic acid or highly dispersed absorbent polymers. Suitable granulated adsorptive carriers are porous types, for example pumice, broken brick, sepiolite or bentonite; and suitable non-sorbent carriers are materials such as calcite or sand. In addition, a great number of pregranulated materials of inorganic or organic nature can be used, e.g. especially dolomite or pulverised plant residues. Phospholipids are particularly preferred.

Depending on the nature of the compound of the formula I to be formulated, suitable surface-active compounds are nonionic, cationic and/or anionic surfactants having good emusifying, dispersing and wetting properties. The term "surfactants" will also be understood as comprising mixtures of surfactants.

Suitable anionic surfactants can be both water-soluble soaps and water-soluble synthetic surface-active compounds.

Suitable soaps are the alkali metal salts, alkaline earth metal salts or unsubstituted or substituted ammonium salts of higher fatty acids ($C_{10}$–$C_{22}$), e.g. the sodium or potassium salts of oleic or stearic acid, or of natural fatty acid mixtures which can be obtained e.g. from coconut oil or tallow oil. Mention may also be made of fatty acid methyltaurin salts.

More frequently, however, so-called synthetic surfactants are used, especially fatty sulfonates, fatty sulfates, sulfonated benzimidazole derivatives or alkylarylsulfonates.

The fatty sulfonates or sulfates are usually in the form of alkali metal salts, alkaline earth metal salts or unsubstituted or substituted ammoniums salts and contain a $C_8$-$C_{22}$alkyl radical which also includes the alkyl moiety of acyl radicals, e.g. the sodium or calcium salt of lignosulfonic acid, of dodecylsulfate or of a mixture of fatty alcohol sulfates obtained from natural fatty acids. These compounds also comprise the salts of sulfuric acid esters and sulfonic acids of fatty alcohol/ethylene oxide adducts. The sulfonated benzimidazole derivatives preferably contain 2 sulfonic acid groups and one fatty acid radical containing 8 to 22 carbon atoms. Examples of alkylarylsulfonates are the sodium, calcium or triethanolamine salts of dodecylbenzenesulfonic acid, dibutylnaphthalenesulfonic acid, or of a naphthalenesulfonic acid/formaldehyde condensation product. Also suitable are corresponding phosphates, e.g. salts of the phosphoric acid ester of an adduct of p-nonylphenol with 4 to 14 moles of ethylene oxide.

Non-ionic surfactants are preferably polyglycol ether derivatives of aliphatic or cycloaliphatic alcohols, or saturated or unsaturated fatty acids and alkylphenols, said derivatives containing 3 to 30 glycol ether groups and 8 to 20 carbon atoms in the (aliphatic) hydrocarbon moiety and 6 to 18 carbon atoms in the alkyl moiety of the alkylphenols.

Further suitable non-ionic surfactants are the water-soluble adducts of polyethylene oxide with polypropylene glycol, ethylenediamine propylene glycol and alkylpolypropylene glycol containing 1 to 10 carbon atoms in the alkyl chain, which adducts contain 20 to 250 ethylene glycol ether groups and 10 to 100 propylene glycol ether groups. These compounds usually contain 1 to 5 ethylene glycol units per propylene glycol unit.

Representative examples of non-ionic surfactants are nonylphenolpolyethoxyethanols, castor oil polyglycol ethers, polypropylene/polyethylene oxide adducts, tributylphenoxypolyethoxyethanol, polyethylene glycol and octylphenoxyethoxyethanol. Fatty acid esters of polyoxyethylene sorbitan and polyoxyethylene sorbitan trioleate are also suitable non-ionic surfactants.

Cationic surfactants are preferably quaternary ammonium salts which contain, as N-substituent, at least one $C_8$-$C_{22}$alkyl radical and, as further substituents, lower unsubstituted or halogenated alkyl, benzyl or lower hydroxyalkyl radicals. The salts are preferably in the form of halides, methylsulfates or ethylsulfates, e.g. stearyltrimethylammonium chloride or benzyldi(2-chloroethyl)ethylammonium bromide.

The surfactants customarily employed in the art of formulation are described e.g. in "McCutcheon's Detergents and Emulsifiers Annual", MC Publishing Corp. Ridgewood, N.J., 1979, and Sisley and Wood, "Encyclopedia of Surface Active Agents", Chemical Publishing Co., Inc. New York, 1980.

The agrochemical compositions usually contain 0.1 to 99%, preferably 0.1 to 95%, of a compound of the formula I, 1 to 99% of a solid or liquid adjuvant, and 0 to 25%, preferably 0.1 to 25%, of a surfactant.

Preferred formulations are composed in particular of the following constituents (% = percentage by weight):

Solutions

| | |
|---|---|
| active ingredient: | 5 to 95%, preferably 10 to 80% |
| solvent: | 95 to 5%, preferably 90 to 0% |
| surfactants: | 1 to 30%, preferably 2 to 20% |
| Emulsifiable concentrates | |
| active ingredient: | 10 to 50%, preferably 10 to 40% |
| surfactant: | 5 to 30%, preferably 10 to 20% |
| liquid carrier: | 20 to 95%, preferably 40 to 80% |
| Dusts | |
| active ingredient: | 0.5 to 10%, preferably 2 to 8% |
| solid carrier: | 99.5 to 90%, preferably 98 to 92% |
| Suspension concentrates | |
| active ingredient: | 5 to 75%, preferably 10 to 50% |
| water: | 94 to 25%, preferably 90 to 30% |
| surfactant: | 1 to 40%, preferably 2 to 30% |
| Wettable powders | |
| active ingredient | 5 to 90%, preferably 10 to 80%, and most preferably 20 to 60%, |
| surfactant: | 0.5 to 20%, preferably 1 to 15% |
| solid carrier: | 5 to 90%, preferably 30 to 70% |
| Granulates | |
| active ingredient: | 0.5 to 30%, preferably 3 to 15% |
| solid carrier: | 99.5 to 70%, preferably 97 to 85%. |

Whereas commercial products will be preferably formulated as concentrates, the end user will normally employ dilute formulations. The formulations can be diluted to a concentration as low as 0.001%.

The compositions may also contain further ingredients, such as stabilisers, antifoams, viscosity regulators, binders, tackifiers as well as fertilisers or other active ingredients in order to obtain special effects.

Such agrochemical compositions also constitute an object of the present invention.

The invention is illustrated in more detail by the following Examples, without implying any restriction to what is described therein. Parts and percentages are by weight.

PREPARATORY EXAMPLES

EXAMPLE 1

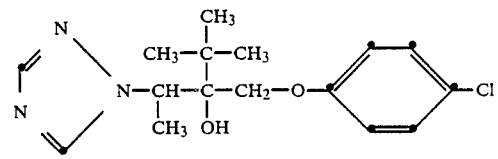

1-(4-chlorophenoxy)-2-tert-butyl-2-hydroxy-3-methyl-3-(1H-1,2,4-triazol-1-yl)propane (compound 1)

(a) 2-tert-Butyl-2-[1-(1H-1,2,4-triazol-1-yl)ethyl]-oxirane: With stirring, a mixture of 23 g (0.127 mole) of 1-(1H-1,2,4-triazol-1-yl)ethyl-tert-butyl ketone, 33 g (0.15 mole) of trimethyloxosulfonium iodide, 1 g (0.0031 mole) of tetrabutylammonium bromide, 30 ml of aqueous potassium hydroxide solution and 80 ml of toluene is heated for 24 hours to 90° C. After the mixture has cooled, the organic phase is separated and washed with water, dried and concentrated, affording 16 g (96% of theory of 2-tert-butyl-2-[1-(1H-1,2,4-triazol-1-yl)ethyl]-oxirane with a boiling point of 68°-70° C./0.01 mbar. (Compound 401).

(b) A mixture of 16 g (0.082 mole) of 2-tert-butyl-2-[1-(1H-1,2,4-triazol-1-yl)ethyl]-oxirane, 12.6 g (0.106 mole) of 4-chlorophenyl, 1 g (0.024 mole) of lithium hydroxide hydrate and 50 ml of diethylene glycol dimethyl ether is heated for 12 hours to 150° C. After it has cooled, the reaction mixture is poured into ice/water and extracted with ethyl acetate. The organic phase is dried and concentrated, affording 12 g (51.3% of theory) of 1-(4-chlorophenoxy)-2-tert-butyl-2-hydroxy-3-methyl-3-(1H-1,2,4-triazol-1-yl)propane in the form of a 1:1 mixture of diastereoisomers with a melting point of 80°–104° C. (compound 1).

Analysis: $C_{16}H_{22}ClN_3O$

| | | | | |
|---|---|---|---|---|
| calc.: | C 59.35% | H 6.85% | N 12.98% | Cl 10.85% |
| found: | C 59.6% | H 7.0% | N 12.8% | Cl 10.5% |

The separation of the diastereoisomers is effected by chromatography over silica gel with a 4:1 mixture of ethyl acetate/toluene as eluant, affording two diastereoisomers with melting points of 109°–110° C. (compound 2) and 128°–130° C. (compound 3) respectively.

EXAMPLE 2

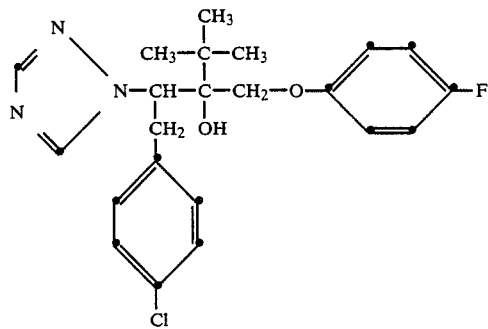

1-(4-fluorophenoxy)-2-tert-butyl-2-hydroxy-3-(4-chlorobenzyl)-3-(1H-1,2,4-triazol-1-yl)propane (compound 150)

(a) 2-tert-Butyl-2-[1-(1H-1,2,4-triazol-1-yl)-2-(4-chlorophenyl)ethyl]-oxirane 3.5 g of 55% sodium hydride are dispersed in hexane under nitrogen. Excess hexane is removed by decantation and then 60 ml of dimethylsulfoxide and 17.6 g of trimethylsulfoxonium iodide (in portions) are added. A solution of 15 g of 2-(1H-1,2,4-triazol-1-yl)-1-(4-chlorophenyl)-4,4-dimethylpentan-2-one in 30 ml of tetrahydrofuran is then added dropwise to the above mixture and the reaction mixture is stirred for 5 hours at 70° C. After it has cooled, the mixture is poured into ice-water and extracted with ethyl acetate. The organic phase is washed with water and a saturated solution of sodium chloride, dried and concentrated. The crude product is chromatographed over silica gel with a 3:2 mixture of toluene/ethyl acetate as eluant, affording 6.9 g of an approximately 1:1 mixture of diastereoisoomers of 2-tert-butyl-2-[1-(1H-1,2,4-triazol-1-yl)-2-(4-chlorophenyl)ethyl]-oxirane in the form of a resin (compound 413).

(b) A mixture of 15.3 g of 2-tert-butyl-2-[1-(1H-1,2,4-triazol-1-yl)-2-(4-chlorophenyl)ethyl]-oxirane, 5.6 g of 4-fluorophenyl, 0.1 g of lithium hydroxide hydrate and 60 ml of diethylene glycol dimethyl ether is heated for 18 hours to reflux. After it has cooled, the reaction mixture is poured into ice-water and extracted with ethyl acetate. The combined organic phases are washed with 2N sodium hydroxide solution, water and a saturated solution of sodium chloride, dried and concentrated. Crystallisation from a mixture of ether/hexane yields 3.5 g of 1-(4-fluorophenoxy)-2-tert-butyl-2-hydroxy-3-(4-chlorobenzyl)-3-(1H-1,2,4-triazol-1-yl)propane with a melting point of 104°–105° C. (compound 150).

Analysis: $C_{22}H_{25}ClFN_3O_2$

| | | | | | |
|---|---|---|---|---|---|
| calculated: | C 64.26% | H 5.86% | N 9.78% | Cl 8.25% | F 4.42% |
| found: | C 63.5% | H 5.9% | N 10.2% | Cl 8.5% | F 4.6% |

EXAMPLE 3

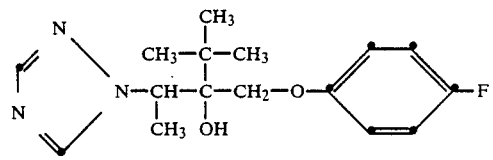

1-(4-fluorophenoxy)-2-tert-butyl-2-hydroxy-3-methyl-3-(1H-1,2,4-triazol-1-yl)propane (compound 18)

A mixture of 10.0 g of 2-tert-butyl-2-[1-(1H-1,2,4-triazol-1-yl)ethyl]-oxirane, 6.4 g of 4-fluorophenol and 0.1 g of lithium hydroxide hydrate in 10 ml of diethylene glycol dimethyl ether is heated for 18 hours to 150° C. After it has cooled, the reaction mixture is poured into ice-water and extracted with ether. The organic phase is washed with water and a saturated solution of sodium chloride, dried and concentrated. Chromatography over silica gel with a 3:1 mixture of ethyl acetate/toluene as eluant yields 11.0 g of 1-(4-fluorophenoxy)-2-tert-butyl-2-hydroxy-3-methyl-3-(1H-1,2,4-triazol-1-yl)propane with a melting point of 85°–100° C. (compound 18).

Analysis: $C_{16}H_{22}FN_3O_2$

| | | | | |
|---|---|---|---|---|
| calculated: | C 62.52% | H 7.22% | N 13.67% | F 6.18% |
| found: | C 62.6% | H 7.2% | N 13.7% | F 6.3% |

EXAMPLE 4

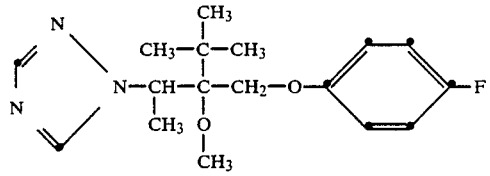

1-(4-fluorophenoxy)-2-tert-butyl-2-methoxy-3-methyl-3-(1H-1,2,4-triazol-1-yl)propane (compound 21)

1.7 g of 52% sodium hydride are dispersed in hexane. After dispersion, excess hexane is removed and the sodium hydride dispersion is taken up in 100 ml of tetrahydrofuran. To this mixture are added 10.0 g of the 1-(4-fluorophenoxy)-2-tert-butyl-2-methoxy-3-methyl-3-(1H-1,2,4-triazol-1-yl)propane obtained in Example 3. The reaction mixture is subsequently heated to 60° C. and kept at this temperature until no more hydrogen gas evolves. Then 5.7 g of methyl iodide are added and the mixture is stirred for 18 hours at 20°–25° C. The reaction mixture is poured into ice-water and extracted with ethyl acetate. The organic phase is washed with water and a saturated solution of sodium chloride, dried and concentrated. The residue is chromatographed over silica gel with a mixture of hexane/ethyl acetate as eluant, affording 7.2 g of 1-(4-fluorophenoxy)-2-tert-butyl-2-methoxy-3-methyl-3-(1H-1,2,4-triazol-1-yl)propane in the form of a highly viscous yellow oil (compound 21). The compounds listed in the following tables are prepared in corresponding manner:

TABLE 1

$$\begin{array}{c} \overset{N}{\underset{N}{\diagdown}}N-\overset{R_3}{\underset{R_2}{\overset{|}{C}}}-\overset{R_4}{\underset{\underset{R_6}{\overset{|}{O}}}{\overset{|}{C}}}-CH_2-O-R_5 \end{array}$$

| No. | $R_2$ | $R_3$ | $R_4$ | $R_5$ | $R_6$ | Physical data |
|---|---|---|---|---|---|---|
| 1 | $CH_3$ | H | $t\text{-}C_4H_9$ | $4\text{-}Cl\text{-}C_6H_4-$ | H | m.p. 90–104° C. |
| 2 | $CH_3$ | H | $t\text{-}C_4H_9$ | $4\text{-}Cl\text{-}C_6H_4-$ | H | diastereo-isomer I m.p. 109–110° C. |
| 3 | $CH_3$ | H | $t\text{-}C_4H_9$ | $4\text{-}Cl\text{-}C_6H_4-$ | H | diastereo-isomer II m.p. 128–130° C. |
| 4 | $CH_3$ | H | $t\text{-}C_4H_9$ | $4\text{-}Cl\text{-}C_6H_4-$ | $CH_3$ | highly viscous oil |
| 5 | $CH_3$ | H | $t\text{-}C_4H_9$ | $4\text{-}Cl\text{-}C_6H_4-$ | $-CO-CH_3$ | |
| 6 | $CH_3$ | H | $t\text{-}C_4H_9$ | $4\text{-}Cl\text{-}C_6H_4-$ | $-CH_2-C_6H_5$ | |
| 7 | $CH_3$ | H | $t\text{-}C_4H_9$ | $4\text{-}Cl\text{-}C_6H_4-$ | $4\text{-}Cl\text{-}C_6H_4-CH_2-$ | |
| 8 | $CH_3$ | H | $t\text{-}C_4H_9$ | $4\text{-}Cl\text{-}C_6H_4-$ | $-CO-N(CH_3)_2$ | |
| 9 | $CH_3$ | H | $t\text{-}C_4H_9$ | $4\text{-}Cl\text{-}C_4H_4-$ | $-CO-$ | |
| 10 | $CH_3$ | H | $t\text{-}C_4H_9$ | $4\text{-}Cl\text{-}C_6H_4-$ | $-CH_2-CN$ | |
| 11 | $CH_3$ | H | $t\text{-}C_4H_9$ | $4\text{-}Cl\text{-}C_6H_4-$ | $-SO_2-CH_3$ | |
| 12 | $CH_3$ | H | $t\text{-}C_4H_9$ | $4\text{-}Cl\text{-}C_6H_4-$ | $-SO_2-N(CH_3)_2$ | |
| 13 | $CH_3$ | H | $t\text{-}C_4H_9$ | $4\text{-}Cl\text{-}C_6H_4-$ | $-CH_2-CH=CH_2$ | |
| 14 | $CH_3$ | H | $t\text{-}C_4H_9$ | $4\text{-}Cl\text{-}C_6H_4-$ | $-CO-CH_2-OCH_3$ | |
| 15 | $CH_3$ | H | $t\text{-}C_4H_9$ | $4\text{-}Cl\text{-}C_6H_4$ | $-CO-CH_2-CN$ | |
| 16 | $CH_3$ | H | $t\text{-}C_4H_9$ | $4\text{-}Cl\text{-}C_6H_4-$ | $-CO-C_2H_5$ | |
| 17 | $CH_3$ | H | $t\text{-}C_4H_9$ | $4\text{-}Cl\text{-}C_6H_4-$ | $-CO-C_3H_7\text{-}n$ | |
| 18 | $CH_3$ | H | $t\text{-}C_4H_9$ | $4\text{-}F\text{-}C_6H_4$ | H | m.p. 85–100° C. |
| 19 | $C_2H_5$ | H | $t\text{-}C_4H_9$ | $4\text{-}F\text{-}C_6H_4-$ | H | oil |
| 20 | $C_2H_5$ | H | $t\text{-}C_4H_9$ | $4\text{-}Cl\text{-}C_6H_4-$ | H | m.p. 97–99° C. |
| 21 | $CH_3$ | H | $t\text{-}C_4H_9$ | $4\text{-}F\text{-}C_6H_4-$ | $CH_3$ | highly viscous oil |
| 22 | $CH_3$ | H | $t\text{-}C_4H_9$ | $4\text{-}F\text{-}C_6H_4-$ | $-CO-CH_3$ | |
| 23 | $CH_3$ | H | $t\text{-}C_4H_9$ | $4\text{-}F\text{-}C_6H_4-$ | $-CH_2-C_6H_5$ | |
| 24 | $CH_3$ | H | $t\text{-}C_4H_9$ | $4\text{-}F\text{-}C_6H_4-$ | $4\text{-}Cl\text{-}C_6H_4-CH_2-$ | |
| 25 | $CH_3$ | H | $t\text{-}C_4H_9$ | $4\text{-}F\text{-}C_6H_4-$ | $-CO-NHCH_3$ | |
| 26 | $CH_3$ | H | $t\text{-}C_4H_9$ | $4\text{-}Cl\text{-}C_6H_4-$ | $-CO-NHCH_3$ | |
| 27 | $CH_3$ | H | $t\text{-}C_4H_9$ | $4\text{-}F\text{-}C_6H_4-$ | $-CO-N(CH_3)_2$ | |
| 28 | $CH_3$ | H | $t\text{-}C_4H_9$ | $4\text{-}F\text{-}C_6H_4-$ | $-CO-N(CH_3)OCH_3$ | |
| 29 | $CH_3$ | H | $t\text{-}C_4H_9$ | $4\text{-}F\text{-}C_6H_4-$ | $-CH_2-CN$ | |
| 30 | $CH_3$ | H | $t\text{-}C_4H_9$ | $4\text{-}F\text{-}C_6H_4-$ | $-SO_2-CH_3$ | |
| 31 | $CH_3$ | H | $t\text{-}C_4H_9$ | $4\text{-}F\text{-}C_6H_4-$ | $-CH_2-COOCH_3$ | |
| 32 | $CH_3$ | H | $t\text{-}C_4H_9$ | $4\text{-}F\text{-}C_6H_4-$ | $-SO_2-N(CH_3)_2$ | |
| 33 | $CH_3$ | H | $t\text{-}C_4H_9$ | $4\text{-}F\text{-}C_6H_4-$ | $-CH_2-CH=CH_2$ | |
| 34 | $CH_3$ | H | $t\text{-}C_4H_9$ | $4\text{-}F\text{-}C_6H_4-$ | $-CO-CH_2-OCH_3$ | |
| 35 | $CH_3$ | H | $t\text{-}C_4H_9$ | $4\text{-}F\text{-}C_6H_4-$ | $-CO-CH_2-CN$ | |
| 36 | $CH_3$ | H | $t\text{-}C_4H_9$ | $4\text{-}F\text{-}C_6H_4-$ | $-CO-C_2H_5$ | |
| 37 | $CH_3$ | H | $t\text{-}C_4H_9$ | $4\text{-}F\text{-}C_6H_4-$ | $-CO-C_3H_7\text{-}n$ | |
| 38 | $CH_3$ | H | $t\text{-}C_4H_9$ | $4\text{-}Br\text{-}C_6H_4-$ | H | m.p. 90–98° C. |
| 39 | $C_2H_5$ | H | $t\text{-}C_4H_9$ | $4\text{-}Br\text{-}C_6H_4-$ | H | oil |
| 40 | $C_2H_5$ | $CH_3$ | $t\text{-}C_4H_9$ | $4\text{-}Br\text{-}C_6H_4-$ | H | |
| 41 | $C_2H_5$ | $CH_3$ | $t\text{-}C_4H_9$ | $4\text{-}F\text{-}C_6H_4-$ | H | |
| 42 | $C_2H_5$ | $CH_3$ | $t\text{-}C_4H_9$ | $4\text{-}Cl\text{-}C_6H_4-$ | H | |
| 43 | $CH_3$ | H | $t\text{-}C_4H_9$ | $4\text{-}Br\text{-}C_6H_4-$ | $CH_3$ | oil |
| 44 | $CH_3$ | H | $t\text{-}C_4H_9$ | $4\text{-}Br\text{-}C_6H_4-$ | $-CO-CH_3$ | |
| 45 | $CH_3$ | H | $t\text{-}C_4H_9$ | $4\text{-}Br\text{-}C_6H_4-$ | $-CH_2-C_6H_5$ | |
| 46 | $CH_3$ | H | $t\text{-}C_4H_9$ | $4\text{-}Br\text{-}C_6H_4-$ | $4\text{-}Cl\text{-}C_6H_4-CH_2-$ | |
| 47 | $CH_3$ | H | $t\text{-}C_4H_9$ | $4\text{-}Br\text{-}C_6H_4-$ | $-CO-NH-CH_3$ | |
| 48 | $CH_3$ | H | $t\text{-}C_4H_9$ | $4\text{-}Br\text{-}C_6H_4$ | $-CO-N(CH_3)_2$ | |
| 49 | $CH_3$ | H | $t\text{-}C_4H_9$ | $4\text{-}Br\text{-}C_6H_4-$ | $-CO-N(CH_3)OCH_3$ | |
| 50 | $CH_3$ | H | $t\text{-}C_4H_9$ | $4\text{-}Br\text{-}C_6H_4-$ | $-CH_2-CO$ | |
| 51 | $CH_3$ | H | $t\text{-}C_4H_9$ | $4\text{-}Br\text{-}C_6H_4-$ | $-CH_2-CH=CH_2$ | |
| 52 | $CH_3$ | H | $t\text{-}C_4H_9$ | $4\text{-}Br\text{-}C_6H_4-$ | $-CO-CH_2-OCH_3$ | |
| 53 | $CH_3$ | H | $t\text{-}C_4H_9$ | $4\text{-}Br\text{-}C_6H_4-$ | $-SO_2-CH_3$ | |
| 54 | $CH_3$ | H | $t\text{-}C_4H_9$ | $4\text{-}Br\text{-}C_6H_4-$ | $-SO_2-N(CH_3)_2$ | |
| 55 | $CH_3$ | H | $t\text{-}C_4H_9$ | $4\text{-}Br\text{-}C_6H_4-$ | $-CO-CH_2-CH$ | |
| 56 | $CH_3$ | H | $t\text{-}C_4H_9$ | $4\text{-}Br\text{-}C_6H_4-$ | $-CO-C_2H_5$ | |

TABLE 1-continued

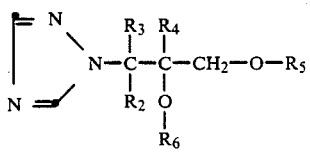

| No. | R_2 | R_3 | R_4 | R_5 | R_6 | Physical data |
|---|---|---|---|---|---|---|
| 57 | $CH_3$ | H | $t-C_4H_9$ | $4-Br-C_6H_4-$ | $-CO-C_3H_7-n$ | |
| 58 | $CH_3$ | H | $t-C_4H_9$ | $C_6H_5-$ | H | semi-crystalline |
| 59 | $CH_3$ | H | $t-C_4H_9$ | $C_6H_5-$ | $CH_3$ | |
| 60 | $CH_3$ | H | $t-C_4H_9$ | $C_6H_5-$ | $-CO-CH_3$ | |
| 61 | $CH_3$ | H | $t-C_4H_9$ | $4-CH_3-C_6H_4-$ | H | diastereoisomer II m.p. 101-102° C. |
| 62 | $CH_3$ | H | $t-C_4H_9$ | $2-Cl-4-Cl-C_6H_3-$ | H | m.p. 136-139° C. |
| 63 | $CH_3$ | H | $t-C_4H_9$ | $2-Cl-3-Cl-C_6H_3-$ | H | m.p. 147-148° C. |
| 64 | $CH_3$ | H | $t-C_4H_9$ | $4-CF_3-C_6H_4-$ | H | |
| 65 | $CH_3$ | H | $t-C_4H_9$ | $3-Cl-5-Cl-C_6H_3-$ | H | |
| 66 | $CH_3$ | H | $t-C_4H_9$ | $2-CH_3-3-CH_3-C_6H_3-$ | H | m.p. 171-172° C. |
| 67 | $CH_3$ | H | $t-C_4H_9$ | $3-Cl-C_6H_4-$ | H | |
| 68 | $CH_3$ | H | $t-C_4H_9$ | $2-Cl-C_6H_4-$ | H | m.p. 143-145° C. |
| 69 | $CH_3$ | H | $t-C_4H_9$ | $2-Cl-6-Cl-C_6H_3-$ | H | m.p. 101-104° C. |
| 70 | $CH_3$ | H | $t-C_4H_9$ | $4-OCH_3-C_6H_4-$ | H | m.p. 88-92° C. |
| 71 | $CH_3$ | H | $t-C_4H_9$ | $4-SCHF_2-C_6H_4-$ | H | |
| 72 | $CH_3$ | H | $t-C_4H_9$ | $4-OCHF_2-C_6H_4-$ | H | |
| 73 | $CH_3$ | H | $t-C_4H_9$ | $4-OCF_3-C_6H_4-$ | H | diastereoisomer I m.p. 98-99° C. |
| 74 | $CH_3$ | H | $t-C_4H_9$ | $4-NO_2-C_6H_4-$ | H | m.p. 107-108° C. |
| 75 | $C_2H_5$ | H | $t-C_4H_9$ | $4-Cl-C_6H_4-$ | $CH_3$ | |
| 76 | $C_2H_5$ | H | $t-C_4H_9$ | $4-Cl-C_6H_4-$ | $-CO-CH_3$ | |
| 77 | $C_2H_5$ | H | $t-C_4H_9$ | $4-Cl-C_6H_4-$ | $-CH_2-C_6H_5$ | |
| 78 | $C_2H_5$ | H | $t-C_4H_9$ | $4-F-C_6H_4-$ | $CH_3$ | |
| 79 | $C_2H_5$ | H | $t-C_4H_9$ | $4-F-C_6H_4-$ | $-CO-CH_3$ | |
| 80 | $C_2H_5$ | H | $t-C_4H_9$ | $4-F-C_6H_4-$ | $-CO-N(CH_3)_2$ | |
| 81 | $C_2H_5$ | H | $t-C_4H_9$ | $4-Br-C_6H_4-$ | $CH_3$ | |
| 82 | $C_2H_5$ | H | $t-C_4H_9$ | $4-Br-C_6H_4-$ | $-CO-CH_3$ | |
| 83 | $C_2H_5$ | H | $t-C_4H_9$ | $4-Br-C_6H_4-$ | $-CH_2-C_6H_5$ | |
| 84 | $n-C_3H_7$ | H | $t-C_4H_9$ | $4-Br-C_6H_4-$ | H | oil |
| 85 | $n-C_3H_7$ | H | $t-C_4H_9$ | $4-Br-C_6H_4-$ | $-CO-CH_3$ | |
| 86 | $n-C_3H_7$ | H | $t-C_4H_9$ | $4-Cl-C_6H_4-$ | H | oil |
| 87 | $n-C_3H_7$ | H | $t-C_4H_9$ | $4-Cl-C_6H_4-$ | $CH_3$ | |
| 88 | $n-C_3H_7$ | H | $t-C_4H_9$ | $4-Cl-C_6H_4-$ | $-CO-CH_3$ | |
| 89 | $n-C_3H_7$ | H | $t-C_4H_9$ | $4-F-C_6H_4-$ | H | oil |
| 90 | $n-C_3H_7$ | H | $t-C_4H_9$ | $4-F-C_6H_4-$ | $CH_3$ | |
| 91 | $n-C_3H_7$ | H | $t-C_4H_9$ | $4-F-C_6H_4-$ | $-CH_2-C_6H_5$ | |
| 92 | $n-C_3H_7$ | H | $t-C_4H_9$ | $4-F-C_6H_4-$ | $-CO-CH_3$ | |
| 93 | $n-C_3H_7$ | H | $t-C_4H_9$ | $4-CH_3-C_6H_4-$ | H | oil |
| 94 | $n-C_3H_7$ | H | $t-C_4H_9$ | $4-OCHF_2-C_6H_4-$ | H | |
| 95 | $n-C_3H_7$ | H | $t-C_4H_9$ | $C_6H_5$ | H | oil |
| 96 | $n-C_3H_7$ | H | $t-C_4H_9$ | $C_6H_5$ | $CH_3$ | |
| 97 | $n-C_4H_9$ | H | $t-C_4H_9$ | $4-Cl-C_6H_4-$ | H | |
| 98 | $n-C_4H_9$ | H | $t-C_4H_9$ | $4-Br-C_6H_4-$ | H | |
| 99 | $n-C_4H_9$ | H | $t-C_4H_9$ | $4-F-C_6H_4-$ | H | |
| 100 | $n-C_4H_9$ | H | $t-C_4H_9$ | $4-CH_3-C_6H_4-$ | H | |
| 101 | $n-C_4H_9$ | H | $t-C_4H_9$ | $C_6H_5$ | H | |
| 102 | $C_6H_5-CH_2-$ | H | $t-C_4H_9$ | $4-Cl-C_6H_5-$ | H | |
| 103 | $C_6H_5-CH_2-$ | H | $t-C_4H_9$ | $4-F-C_6H_5-$ | H | |
| 104 | $C_6H_5-CH_2-$ | H | $t-C_4H_9$ | $4-Br-C_6H_5-$ | H | |
| 105 | $CH_2=CH-CH_2-$ | H | $t-C_4H_9$ | $4-Cl-C_6H_4-$ | H | |
| 106 | $CH_2=CH-CH_2-$ | H | $t-C_4H_9$ | $4-F-C_6H_4-$ | H | |
| 107 | $4-Cl-C_6H_4-CH_2-$ | H | $t-C_4H_9$ | $4-Cl-C_6H_4-$ | H | m.p. 128-129° C. |
| 108 | $CH_3$ | H | $-C(CH_3)_2-C_2H_5$ | $4-Cl-C_6H_4-$ | H | |
| 109 | $CH_3$ | H | $-C(CH_3)_2-C_2H_5$ | $4-Cl-C_6H_4-$ | $CH_3$ | |
| 110 | $CH_3$ | H | $-C(CH_3)_2-C_2H_5$ | $4-Cl-C_6H_4-$ | $-CO-CH_3$ | |
| 111 | $CH_3$ | H | $-C(CH_3)_2-C_2H_5$ | $4-Cl-C_6H_4-$ | $-CH_2-C_6H_5$ | |
| 112 | $CH_3$ | H | $-C(CH_3)_2-C_2H_5$ | $4-F-C_6H_4-$ | H | |
| 113 | $CH_3$ | H | $-C(CH_3)_2-C_2H_5$ | $4-Br-C_6H_4-$ | H | |

TABLE 1-continued $$\begin{array}{c} \stackrel{N}{\underset{N}{\nearrow}} N-\stackrel{R_3}{\underset{R_2}{\overset{|}{C}}}-\stackrel{R_4}{\underset{\stackrel{|}{O}}{\overset{|}{C}}}-CH_2-O-R_5 \\ \phantom{xxxxxxxxxxx} \stackrel{|}{R_6} \end{array}$$

| No. | $R_2$ | $R_3$ | $R_4$ | $R_5$ | $R_6$ | Physical data |
|---|---|---|---|---|---|---|
| 114 | $CH_3$ | H | $-C(CH_3)_2-C_2H_5$ | $4-CH_3-C_6H_4-$ | H | |
| 115 | $CH_3$ | H | $i-C_3H_7$ | $4-Cl-C_6H_4-$ | H | $n_D^{30}$ 1.5323 |
| 116 | $CH_3$ | H | $i-C_3H_7$ | $4-Cl-C_6H_4-$ | $CH_3$ | |
| 117 | $CH_3$ | H | $i-C_3H_7$ | $4-Cl-C_6H_4-$ | $-CO-CH_3$ | |
| 118 | $CH_3$ | H | $t-C_4H_9$ | $n-C_4H_9$ | H | |
| 119 | $CH_3$ | H | $t-C_4H_9$ | $n-C_4H_9$ | $CH_3$ | |
| 120 | $CH_3$ | H | $t-C_4H_9$ | $n-C_4H_9$ | $-CO-CH_3$ | |
| 121 | $CH_3$ | H | $t-C_4H_9$ | $cycl-C_6H_{11}$ | H | |
| 122 | $CH_3$ | H | $t-C_4H_9$ | $cycl-C_6H_{11}$ | $CH_3$ | |
| 123 | $CH_3$ | H | $t-C_4H_9$ | $cycl-C_6H_{11}$ | $-CO-CH_3$ | |
| 124 | $CH_3$ | H | $t-C_4H_9$ | $cycl-C_6H_{11}$ | $-CH_2-C_6H_5$ | |
| 125 | $CH_3$ | H | $t-C_4H_9$ | $CH_3$ | H | m.p. 149–155° C. |
| 126 | $CH_3$ | H | $t-C_4H_9$ | $4-F-C_6H_4-CH_2-$ | H | |
| 127 | $CH_3$ | H | $-C(CH_3)_2-C_6H_5$ | $4-Cl-C_6H_4-$ | H | |
| 128 | $CH_3$ | H | $-C(CH_3)_2-C_6H_5$ | $4-F-C_6H_4-$ | H | |
| 129 | $CH_3$ | H | $-C(CH_3)_2-C_6H_5$ | $4-Br-C_6H_4-$ | H | |
| 130 | $C_2H_5$ | H | $t-C_4H_9$ | $CH_3$ | H | diastereo-isomer I m.p. 116–118° C. |
| 131 | $C_2H_5$ | H | $t-C_4H_9$ | $4-Cl-C_6H_4-$ | H | diastereo-isomer I m.p. 97–99° C. |
| 132 | $CH_3$ | H | $t-C_4H_9$ | $4-Br-C_6H_4-$ | H | diastereo-isomer I m.p. 128–130° C. |
| 133 | $CH_3$ | H | $t-C_4H_9$ | $4-Br-C_6H_4-$ | H | diastereo-isomer II m.p. 90–98° C. |
| 134 | $C_2H_5$ | H | $t-C_4H_9$ | $C_6H_5$ | H | oil |
| 135 | $C_2H_5$ | H | $t-C_4H_9$ | $4-CH_3-C_6H_4-$ | H | oil |
| 136 | $CH_3$ | H | $t-C_4H_9$ | $2-F-C_6H_4-$ | H | m.p. 115–116° C. |
| 137 | $CH_3$ | H | $t-C_4H_9$ | $2-CH_3-4-Cl-C_6H_5-$ | H | m.p. 131–132° C. |
| 138 | $CH_3$ | H | $t-C_4H_9$ | $2-CH_3-C_6H_4-$ | H | m.p. 133–134° C. |
| 139 | $CH_3$ | H | $t-C_4H_9$ | $2-Br-C_6H_4-$ | H | m.p. 148–149° C. |
| 140 | $CH_3$ | H | $i-C_3H_7$ | $4-Br-C_6H_4-$ | H | semi-crystalline |
| 141 | $CH_3$ | H | $i-C_3H_7$ | $4-F-C_6H_4-$ | H | $n_D^{30}$: 1.5091 |
| 142 | $CH_3$ | H | $t-C_4H_9$ | $3-CH_3-C_6H_4-$ | H | m.p. 88–90° C. |
| 143 | $CH_3$ | H | $t-C_4H_9$ | $3-Br-C_6H_4-$ | H | m.p. 102–105° C. |
| 144 | $CH_3$ | H | $t-C_4H_9$ | $4-C_4H_9-t-C_6H_4-$ | H | m.p. 92–95° C. |
| 145 | $CH_3$ | H | $t-C_4H_9$ | $4-OCF_3-C_6H_4-$ | H | diastereo-isomer II m.p. 74–76° C. |
| 146 | $CH_3$ | H | $n-C_6H_{13}$ | $4-Cl-C_6H_4-$ | H | $n_D^{20}$: 1.5248 |
| 147 | $C_2H_5$ | H | $t-C_4H_9$ | $4-OCF_3-C_6H_4-$ | H | viscous oil |
| 148 | $4-F-C_6H_4-CH_2-$ | H | $t-C_4H_9$ | $4-F-C_6H_4-$ | H | resin |
| 149 | $4-F-C_6H_4-CH_2-$ | H | $t-C_4H_9$ | $4-Cl-C_6H_4-$ | H | m.p. 121–122° C. |
| 150 | $4-Cl-C_6H_4-CH_2-$ | H | $t-C_4H_9$ | $4-F-C_6H_4-$ | H | m.p. 104–105° C. |
| 151 | $CH_3$ | H | $i-C_3H_7$ | $4-CH_3-C_6H_4-$ | H | m.p. 68–72° C. |
| 152 | $CH_3$ | H | $1-CH_3-cycl.C_3H_4-$ | $4-F-C_6H_4-$ | H | b.p. 150° C. 0,1 mb |
| 153 | $CH_3$ | H | $i-C_4H_9$ | $4-F-C_6H_4-$ | H | $n_D^{35}$: 1.5125 |
| 154 | $CH_3$ | H | $i-C_4H_9$ | $4-Cl-C_6H_4-$ | H | $n_D^{35}$: 1.5310 |
| 155 | $CH_3$ | $CH_3$ | $CH_3$ | $4-Cl-C_6H_4-$ | H | m.p. 84–86° C. |
| 156 | $CH_3$ | H | $t-C_4H_9$ | $4-COOCH_3-C_6H_4-$ | H | |

TABLE 1-continued

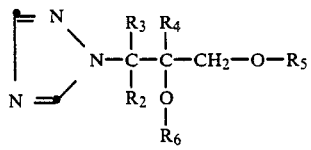

| No. | $R_2$ | $R_3$ | $R_4$ | $R_5$ | $R_6$ | Physical data |
|---|---|---|---|---|---|---|
| 157 | $CH_3$ | H | $t-C_4H_9$ | $4-N(CH_3)_2-C_6H_4-$ | H | |
| 158 | $CH_3$ | H | $t-C_4H_9$ | $4-(NH-CO-CH_3)-C_6H_4-$ | H | |
| 159 | $4-Cl-C_6H_4-CH_2-$ | H | $t-C_4H_9$ | $CH_3$ | H | |
| 160 | $4-F-C_6H_4-CH_2-$ | H | $t-C_4H_9$ | $CH_3$ | H | highly viscous oil |
| 161 | $2-Cl-4-Cl-C_6H_3-CH_2-$ | H | $t-C_4H_9$ | $4-F-C_6H_4-$ | H | |
| 162 | $2-Cl-4-Cl-C_6H_3-CH_2-$ | H | $t-C_4H_9$ | $4-Cl-C_6H_4-$ | H | |
| 163 | $2-Cl-4-Cl-C_6H_3-CH_2-$ | H | $t-C_4H_9$ | $CH_3$ | H | |
| 164 | $4-F-C_6H_4-CH_2-$ | H | $t-C_4H_9$ | $C_2H_5$ | H | |
| 165 | $4-Cl-C_6H_4-CH_2-$ | H | $t-C_4H_9$ | $C_2H_5$ | H | |
| 166 | $CH_3$ | H | $-CH(CH_3)-C_4H_9-n$ | $C_6H_5$ | H | $n_D^{25}$ 1.5150 |
| 167 | $CH_3$ | H | $-CH(CH_3)-C_4H_9-n$ | $4-F-C_6H_4-$ | H | $n_D^{25}$ 1.5080 |
| 168 | $CH_3$ | H | $-CH(CH_3)-C_4H_9-n$ | $4-Cl-C_6H_4-$ | H | $n_D^{25}$ 1.5160 |
| 169 | $CH_3$ | H | $-CH(CH_3)-C_4H_9-n$ | $4-Br-C_6H_4-$ | H | $n_D^{25}$ 1.5190 |
| 170 | $CH_3$ | H | $-C(CH_3)_2-C_6H_5$ | $4-F-C_6H_4-$ | H | |
| 171 | $CH_3$ | H | $-C(CH_3)_2-C_6H_5$ | $4-Cl-C_6H_4-$ | H | |
| 172 | $CH_3$ | H | $-C(CH_3)_2-C_6H_4-4-Cl$ | $4-F-C_6H_4-$ | H | |
| 173 | $CH_3$ | H | $-C(CH_3)_2-C_6H_4-4-Cl$ | $4-Cl-C_6H_4-$ | H | |
| 174 | $CH_3$ | H | $-CH(C_2H_5)-C_4H_9-n$ | $4-F-C_6H_4-$ | H | |
| 175 | $CH_3$ | H | $-CH(C_2H_5)-C_4H_9-n$ | $4-Cl-C_6H_4-$ | H | |
| 176 | $CH_3$ | H | $-CH(C_2H_5)-C_3H_7-n$ | $4-Cl-C_6H_4-$ | H | |
| 177 | $CH_3$ | H | $-CH(C_2H_5)-C_3H_7-n$ | $4-F-C_6H_4-$ | H | |
| 178 | $CH_3$ | H | $i-C_5H_{11}$ | $4-F-C_6H_4-$ | H | |
| 179 | $CH_3$ | H | $i-C_5H_{11}$ | $4-Cl-C_6H_4-$ | H | |
| 180 | $CH_3$ | H | $i-C_5H_{11}$ | $4-Br-C_6H_4-$ | H | |

TABLE 2

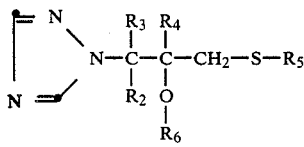

| No. | $R_2$ | $R_3$ | $R_4$ | $R_5$ | $R_6$ | Physical data |
|---|---|---|---|---|---|---|
| 201 | $CH_3$ | H | $t-C_4H_9$ | $4-Cl-C_6H_4-$ | H | highly viscous oil |
| 202 | $CH_3$ | H | $t-C_4H_9$ | $4-F-C_6H_4-$ | H | |
| 203 | $CH_3$ | H | $t-C_4H_9$ | $4-Br-C_6H_4-$ | H | |
| 204 | $C_2H_5$ | H | $t-C_4H_9$ | $4-Cl-C_6H_4-$ | H | |
| 205 | $C_2H_5$ | H | $t-C_4H_9$ | $4-F-C_6H_4-$ | H | |
| 206 | $CH_3$ | H | $i-C_3H_7$ | $4-F-C_6H_4-$ | H | |
| 207 | $CH_3$ | H | $i-C_3H_7$ | $4-F-C_6H_4-$ | $CH_3$ | |

TABLE 2-continued

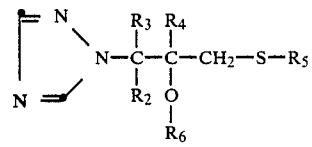

| No. | $R_2$ | $R_3$ | $R_4$ | $R_5$ | $R_6$ | Physical data |
|---|---|---|---|---|---|---|
| 208 | $CH_3$ | H | $t-C_4H_9$ | $4-F-C_6H_4-$ | $CH_3$ | |
| 209 | $CH_3$ | H | $t-C_4H_9$ | $4-Cl-C_6H_4-$ | $CH_3$ | |
| 210 | $C_2H_5$ | H | $t-C_4H_9$ | $4-Cl-C_6H_4-$ | $CH_3$ | |
| 211 | $C_2H_5$ | H | $t-C_4H_9$ | $4-F-C_6H_4-$ | $CH_3$ | |
| 212 | $CH_3$ | H | $t-C_4H_9$ | $n-C_4H_9-$ | H | oil |
| 213 | $CH_3$ | H | $t-C_4H_9$ | $C_6H_5-CH_2-$ | H | |
| 214 | $CH_3$ | H | $t-C_4H_9$ | $4-Cl-C_6H_4-CH_2-$ | H | |
| 215 | $CH_3$ | H | $t-C_4H_9$ | $4-F-C_6H_4-CH_2-$ | H | |

TABLE 3

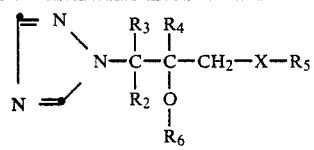

| No. | $R_2$ | $R_3$ | $R_4$ | $R_5$ | $R_6$ | X | Physical data |
|---|---|---|---|---|---|---|---|
| 301 | $CH_3$ | H | $t-C_4H_9$ | $4-Cl-C_6H_4-$ | H | O | m.p. 121–123° C. |
| 302 | $CH_3$ | H | $t-C_4H_9$ | $4-Cl-C_6H_4-$ | H | S | |
| 303 | $CH_3$ | H | $t-C_4H_9$ | $4-Br-C_6H_4-$ | H | O | m.p. 130–132° C. |
| 304 | $CH_3$ | H | $t-C_4H_9$ | $4-Br-C_6H_4-$ | H | S | |
| 305 | $CH_3$ | H | $t-C_4H_9$ | $4-CH_3-C_6H_4-$ | H | O | m.p. 129–130° C. |
| 306 | $CH_3$ | H | $t-C_4H_9$ | $4-CH_3-C_6H_4-$ | H | S | |
| 307 | $CH_3$ | H | $t-C_4H_9$ | $C_6H_5$ | H | O | highly viscous oil |
| 308 | $CH_3$ | H | $t-C_4H_9$ | $C_6H_5$ | H | S | |
| 309 | $CH_3$ | H | $t-C_4H_9$ | $4-F-C_6H_4-$ | H | O | |
| 310 | $CH_3$ | H | $t-C_4H_9$ | $4-F-C_6H_4-$ | H | S | |
| 311 | $CH_3$ | H | $t-C_4H_9$ | $4-F-C_6H_4-$ | $CH_3$ | O | |

TABLE 3-continued

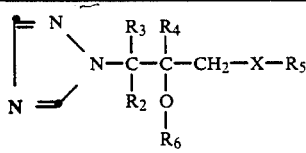

| No. | $R_2$ | $R_3$ | $R_4$ | $R_5$ | $R_6$ | X | Physical data |
|---|---|---|---|---|---|---|---|
| 312 | $CH_3$ | $CH_3$ | $t-C_4H_9$ | $4-F-C_6H_4-$ | H | O | |
| 313 | $CH_3$ | $CH_3$ | $t-C_4H_9$ | $4-F-C_6H_4-$ | $CH_3$ | O | |
| 314 | $CH_3$ | $CH_3$ | $t-C_4H_9$ | $4-F-C_6H_4-$ | $CH_3$ | S | |
| 315 | $CH_3$ | H | $t-C_4H_9$ | $4-F-C_6H_4-$ | $CH_3$ | S | |

TABLE 4

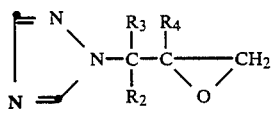

| No. | $R_2$ | $R_3$ | $R_4$ | Physical data |
|---|---|---|---|---|
| 401 | $CH_3$ | H | $t-C_4H_9$ | b.p. 68–70° C., 0.01 mb |
| 402 | $C_2H_5$ | H | $t-C_4H_9$ | b.p. 70–72° C., 0.1 mb |
| 403 | $n-C_3H_7$ | H | $t-C_4H_9$ | b.p. 80–82° C., 0.05 mb |
| 404 | $C_2H_5$ | $CH_3$ | $t-C_4H_9$ | |
| 405 | $CH_3$ | $CH_3$ | $t-C_4H_9$ | oil |
| 406 | $n-C_4H_9$ | H | $t-C_4H_9$ | b.p. 80° C., 0.05 mb |
| 407 | $C_6H_5-CH_2-$ | H | $t-C_4H_9$ | |
| 408 | $CH_2=CH-CH_2-$ | H | $t-C_4H_9$ | |
| 409 | $CH_3$ | H | $-C(CH_3)_2-C_2H_5$ | |
| 410 | $CH_3$ | H | $i-C_3H_7$ | oil |
| 411 | $CH_3$ | H | $-C(CH_3)_2-C_6H_5$ | |
| 412 | $4-Cl-C_6H_4-CH_2-$ | H | $t-C_4H_9$ | resin |
| 413 | $4-F-C_6H_4-CH_2-$ | H | $t-C_4H_9$ | highly viscous oil |
| 414 | $CH_3$ | H | $n-C_6H_{13}$ | oil |
| 415 | $CH_3$ | H | $1-CH_3-cycl-C_3H_4-$ | oil |
| 416 | $CH_3$ | H | $-C(CH_3)_2-C_6H_5$ | |
| 417 | $CH_3$ | H | $-C(CH_3)-C_6H_4-4-Cl$ | |
| 418 | $CH_3$ | H | $-CH(C_2H_5)-C_4H_9-n$ | |
| 419 | $CH_3$ | H | $i-C_5H_{11}$ | |
| 420 | $2-Cl-4-Cl-C_6H_3-CH_2-$ | H | $t-C_4H_9$ | |

FORMULATION EXAMPLES

EXAMPLE 5

| Formulation Examples for liquid active ingredients of the formula I (throughout, percentages are by weight) | | | |
|---|---|---|---|
| (a) Emulsifiable concentrates | (a) | (b) | (c) |
| a compound of formula I | 25% | 40% | 50% |
| calcium dodecylbenzenesulfonate | 5% | 8% | 6% |
| castor oil polyethylene glycol ether (36 moles of ethylene oxide) | 5% | — | — |
| tributylphenol polyethylene glycol ether- (30 moles of ethylene oxide) | — | 12% | 4% |
| cyclohexanone | — | 15% | 20% |
| xylene mixture | 65% | 25% | 20% |

Emulsions of any required concentration can be produced from such concentrates by dilution with water.

| (b) Solutions | (a) | (b) | (c) | (d) |
|---|---|---|---|---|
| a compound of formula I | 80% | 10% | 5% | 95% |
| ethylene glycol monomethyl ether | 20% | — | — | — |
| polyethylene glycol 400 | — | 70% | — | — |
| N-methyl-2-pyrrolidone | — | 20% | — | — |
| epoxidised coconut oil | — | — | 1% | 5% |
| petroleum distillate (boiling range 160–190°) | — | — | 94% | — |

These solution are suitable for application in the form of microdrops.

| (c) Granulates | (a) | (b) |
|---|---|---|
| a compound of formula I | 5% | 10% |
| kaolin | 94% | — |
| highly dispersed silicic acid | 1% | — |
| attapulgite | — | 90% |

The active ingredient is dissolved in methylene chloride, the solution is sprayed onto the carrier, and the solvent is subsequently stripped off in vacuo.

| (d) Dusts | (a) | (b) |
|---|---|---|
| a compound of formula I | 2% | 5% |
| highly dispersed silicic acid | 1% | 5% |
| talcum | 97% | — |
| kaolin | — | 90% |

Ready-for-use dusts are obtained by intimately mixing the carriers with the active ingredient.

EXAMPLE 6

Formulation examples for solid active ingredients of the formula I (throughout, percentages are by weight)

(a) Wettable powders

| | (a) | (b) | (c) |
|---|---|---|---|
| a compound of formula I | 25% | 50% | 75% |
| sodium lignosulfonate | 5% | 5% | — |
| sodium lauryl sulfate | 3% | — | 5% |
| sodium diisobutylnaphthalenesulfonate | — | 6% | 10% |
| octylphenol polyethylene glycol ether (7–8 moles of ethylene oxide) | — | 2% | — |
| highly dispersed silicic acid | 5% | 10% | 10% |
| kaolin | 62% | 27% | — |

The active ingredient is thoroughly mixed with the adjuvants and the mixture is thoroughly ground in a suitable mill, affording wettable powders which can be diluted with water to give suspensions of the desired concentration.

(b) Emulsifiable concentrate

| | |
|---|---|
| a compound of formula I | 10% |
| octylphenol polyethylene glycol ether (4–5 moles of ethylene oxide) | 3% |
| calcium dodecylbenzenesulfonate | 3% |
| castor oil polyglycol ether (36 moles of ethylene oxide) | 4% |
| cyclohexanone | 30% |
| xylene mixture | 50% |

Emulsions of any required concentration can be obtained from this concentrate by dilution with water.

(c) Dusts

| | (a) | (b) |
|---|---|---|
| a compound of formula I | 5% | 8% |
| talcum | 95% | — |
| kaolin | — | 92% |

Ready-for-use dusts are obtained by mixing the active ingredient with the carriers, and grinding the mixture in a suitable mill.

(d) Extruder granulate

| | |
|---|---|
| a compound of formula I | 10% |
| sodium lignosulfonate | 2% |
| carboxymethylcellulose | 1% |
| kaolin | 87% |

The active ingredient is mixed and ground with the adjuvants, and the mixture is subsequently moistened with water. The mixture is extruded and then dried in a stream of air.

(e) Coated granulate

| | |
|---|---|
| a compound of formula I | 3% |
| polyethylene glycol 200 | 3% |
| kaolin | 94% |

The finely ground active ingredient is uniformly applied, in a mixer, to the kaolin moistened with polyethylene glycol. Non-dusty coated granulates are obtained in this manner (f) Suspension concentrate

| | |
|---|---|
| a compound of formula I | 40% |
| ethylene glycol | 10% |
| nonylphenol polyethylene glycol (15 moles of ethylene oxide) | 6% |
| sodium lignosulfonate | 10% |
| carboxymethylcellulose | 1% |
| 37% aqueous formaldehyde solution | 0.2% |
| silicone oil in the form of a 75% aqueous emulsion | 0.8% |
| water | 32% |

The finely ground active ingredient is intimately mixed with the adjuvants, giving a suspension concentrate from which suspensions of any desired concentration can be obtained by dilution with water.

BIOLOGICAL EXAMPLES

EXAMPLE 7

Action against *Puccinia graminis* on wheat (a) Residual-protective action

Wheat plants are treated 6 days after sowing with a spray mixture prepared from a wettable powder formulation of the test compound (0.06%). After 24 hours the treated plants are infected with a uredospore suspension of the fungus. The infected plants are incubated for 48 hours at 95–100% relative humidity and about 20° C. and then stood in a greenhouse at about 22° C. Evaluation of rust pustule development is made 12 days after infection.

(b) Systemic action

Wheat plants are treated 5 days after sowing with a spray mixture prepared from a wettable powder formulation of the test compound (0.006%, based on the volume of the soil). After 48 hours the treated plants are infected with a uredospore suspension of the fungus. The plants are then incubated for 48 hours at 95–100% relative humidity and about 20° C. and then stood in a greenhouse at about 22° C. Evaluation of rust pustule development is made 12 days after infection. Compounds of Table 1 are effective against Puccinia fungi. Puccinia attack is 100% on untreated and infected control plants. Compounds 1 to 3, 18, 19, 20, 38, 39, 83, 86, 89, 95, 125 and 131 and other inhibit Puccinia attack to 0–5%.

EXAMPLE 8

Action against *Cercospora arachidicola* in groundnut plants (a) Residual protective action Groundnut plants 10–15 cm in height are sprayed with a spray mixture (0.02%) prepared from a wettable powder formulations of the test compound, and infected 48 hours later with a conidia suspension of the fungus. The infected plants are incubated for 72 hours at about 21° C. and high humidity and then stood in a greenhouse until the typical leaf specks occur. Evaluation of the fungicidal action is made 12 days after infection and is based on the number and size of the specks.

(b) Systemic action

Groundnut plants 10–15 cm in height are treated with a spray mixture (0.06%) based on the volume of the soil) prepared from the test compound formulated as wettable powder. The treated plants are infected 48 hours later with a conidia suspension of the fungus and incubated for 72 hours at about 21° C. and high humidity.

The infected plants are then stood in a greenhouse and evaluation of infestation is made after 11 days.

Compared with untreated and infected controls (number and size of the specks<100%), Cercospora attack on groundnut plants treated with compounds of Table 1 is greatly reduced. Thus compounds 1 to 3, 18, 19, 20, 38, 39, 83, 89, 95, 125 and 131 inhibit the occurrence of specks in the above tests almost completely (0–10%).

EXAMPLE 9

Action against *Erysiphe graminis* on barley (a) Residual protective action

Barley plants about 8 cm in height are sprayed with a spray mixture (0.02%) prepared from the test compound formulated as a wettable powder. The treated plants are dusted with conidia of the fungus after 3–4 hours. The infected barley plants are then stood in a greenhouse at about 22° C. The extent of the infestation is evaluated after 10 days.

(b) Systemic action

Barley plants about 8 cm in height are treated with a spray mixture (0.006%) based on the volume of the soil) prepared from the test compound formulated as wettable powder. Care is taken that the spray mixture does not come in contact with parts of the plants above the soil. The treated plants are infected 48 hours later with a conidia suspension of the fungus. The infected barley plants are then stood in a greenhouse at about 22° C. and evaluation of infestation is made after 10 days.

Compounds of the formula I are very effective against Erysiphe fungi. Erysiphe attack is 100% on untreated and infected control plants. Among other compounds of Table 1, compounds 1 to 3, 18, 19, 20, 38, 39, 89, 95, 125 and 131 to 133 inhibit fungus attack on barley to 0–5%.

EXAMPLE 10

Residual-protective action against *Venturia inaequalis* on apple shoots

Apple cuttings with 10–20 cm long fresh shoots are sprayed with a spray mixture (0.06%) prepared from a wettable powder formulation of the active ingredient. The plants are infected 24 hours later with a conidia suspension of the fungus. The plants are then incubated for 5 days at 90–100% relative humidity and stood in a greenhouse for a further 10 days at 20°–24° C. Scab infestation is evaluated 15 days after infection. Compounds 1 to 3, 18, 19, 20, 38, 39, 83, 89, 95, 131 and other inhibit attack to less than 10%. Venturia attack on untreated and infected shoots is 100%.

EXAMPLE 11

Action against *Botrytis cinerea* on beans

Residual protective action

Bean plants about 10 cm in height are sprayed with a spray mixture (0.02%) prepared from the test compound formulated as wettable powder. After 48 hours, the treated plants are infected with a conidia suspension of the fungus. The infected plants are incubated for 3 days at 95–100% relative humidity and 21° C., and evaluation of the fungus attack is then made. Many compounds of Table 1 very strongly inhibit fungus attack. At a concentration of 0.02% compounds 1, 125 and 131 to 133 and others are fully effective (attack 0 to 5%). Botrytis attack on untreated and infect bean plants is 100%.

EXAMPLE 12

Growth inhibition of cereals

Summar barley (*Hordeum vulgare*) and summer rye (*Secale*) are sown in sterilised soil in plastic beakers in a greenhouse and watered as required. The cereal shoots are treated about 21 days after sowing with an aqueous spray mixture of a compound of the formula I. The concentration corresponds to 4 and 2.5 kg respectively of active ingredient per hectare. Evaluation of the growth of the cereals is made 10 and 21 days after application. A comparison with untreated controls shows that the growth of cereal plants treated with compounds of the formula I is substantially reduced.

| Compound | Rate of application of a. i. kg/ha | Size of plants compared with control plants (%) (controls = 100%) cereals | |
|---|---|---|---|
| | | barley | rye |
| 1 | 4 | 27 | — |
| 4 | 2.5 | 75 | 46 |
| 18 | 2.5 | 14 | 7 |
| 19 | 2.5 | 21 | 11 |
| 21 | 2.5 | 42 | 31 |
| 38 | 2.5 | 56 | 40 |
| 39 | 2.5 | 88 | 81 |
| 43 | 2.5 | 81 | 73 |
| 61 | 2.5 | 69 | 24 |
| 63 | 2.5 | 72 | 80 |
| 66 | 2.5 | 26 | 30 |
| 68 | 2.5 | 74 | 78 |
| 74 | 2.5 | 37 | 18 |
| 89 | 2.5 | 81 | 81 |
| 115 | 2.5 | 66 | 92 |
| 134 | 2.5 | 50 | 37 |
| 135 | 2.5 | 60 | 55 |
| 136 | 2.5 | 45 | 60 |
| 137 | 2.5 | 47 | 45 |
| 138 | 2.5 | 37 | 40 |

EXAMPLE 13

Growth inhibition of grasses

Seeds of the grasses *Lolium perenne*, *Poa pratensis*, *Festuca ovina*, and *Cynodon dactylon* are sown in plastic dishes filled with an earth/peat/sand mixture (6:3:1), in a greenhouse, and watered as required. The emergent grasses are cut back weekly to a height of about 4 cm and, about 50 days after sowing and 1 day after the last cut, are sprayed with an aqueous spray mixture of a compound of the formula I. The concentration of test compound corresponds to a rate of application of 0.5 and 2.5 kg per hectare respectively. The average growth of the grasses is evaluated 10 and 21 days after application. The evaluation shows that the compounds of Tables 1 to 3 effect a marked reduction in growth.

| Compound | Rate of application a. i. kg/ha | Size of plants compared with control plants (%) (controls = 100%) mixture of grasses |
|---|---|---|
| 1 | 4 | 40 |
| 4 | 2.5 | 47 |
| 18 | 2.5 | 23 |
| 19 | 2.5 | 32 |
| 21 | 2.5 | 38 |
| 38 | 2.5 | 50 |
| 39 | 2.5 | 82 |
| 43 | 2.5 | 76 |

-continued

| Compound | Rate of application a. i. kg/ha | Size of plants compared with control plants (%) (controls = 100%) mixture of grasses |
|---|---|---|
| 61 | 2.5 | 32 |
| 63 | 2.5 | 90 |
| 66 | 2.5 | 55 |
| 68 | 2.5 | 86 |
| 74 | 2.5 | 48 |
| 89 | 2.5 | 76 |
| 115 | 2.5 | 81 |
| 134 | 2.5 | 44 |
| 135 | 2.5 | 44 |
| 136 | 2.5 | 41 |
| 137 | 2.5 | 48 |
| 138 | 2.5 | 38 |

EXAMPLE 14

Increase in yield of soybeans

Soybeans of the "Hark" variety are sown in plastic containers in an earth/peat/sand mixture (6:3:1). The containers are put into a climatic chamber and the plants develop to the 5-6 trefoil leaf stage after about 5 weeks by optimum control of temperature, light, fertiliser addition, and watering. The plants are then sprayed with an aqueous mixture of a compound of the formula I until thoroughly wetted. The rate of application corresponds to 3 kg a.i. per hectare. Evaluation is made about 5 weeks after application. Compared with untreated controls, the compounds of the formula I markedly increase the number of weight of the harvested siliques.

| Compound | No. of siliques compared with controls (%) (control = 100%) | Total weight of siliques compared with controls (%) (controls = 100%) |
|---|---|---|
| 1 | 98 | 103 |
| 18 | 105 | 108 |
| 19 | 107 | 111 |
| 38 | 100 | 104 |
| 134 | 107 | 107 |

EXAMPLE 15

Inhibition of the vegetative growth of soybeans

Soybeans of the "Hark" variety are sown in plastic containers in a 6:3:1: mixture of earth/peat/sand. The containers are put into a greenhouse and watered as required. Fifteen days after sowing, the plants are sprayed wet with an aqueous spray mixture of a compound of the formula I until wet. The rate of application corresponds to 1 to 1.5 kg a.i./ha. Evaluation of the growth of the plants is made 7 and 14 days after application. It is observed that the compounds of tables 1 to 3 substantially inhibit growth.

| Compound | Rate of application a. i. kg/ha | Size of plants compared with controls (%) (controls = 100%) |
|---|---|---|
| 1 | 1 | 9 |
| 4 | 1.5 | 13 |
| 18 | 1.5 | 13 |
| 19 | 1.5 | 31 |
| 21 | 1.5 | 15 |
| 38 | 1.5 | 35 |
| 39 | 1.5 | 31 |
| 43 | 1.5 | 23 |
| 61 | 1.5 | 13 |
| 62 | 1.5 | 87 |
| 66 | 1.5 | 82 |
| 68 | 1.5 | 93 |
| 69 | 1.5 | 87 |
| 70 | 1.5 | 36 |
| 74 | 1.5 | 71 |
| 84 | 1.5 | 23 |
| 89 | 1.5 | 77 |
| 93 | 1.5 | 31 |
| 95 | 1.5 | 77 |
| 134 | 1.5 | 62 |
| 135 | 1.5 | 23 |
| 136 | 1.5 | 27 |
| 137 | 1.5 | 73 |
| 138 | 1.5 | 78 |
| 139 | 1.5 | 100 |

EXAMPLE 16

Growth inhibition of cover crops

Test plants of the varieties Psophocarpus palustris and Centrosema pubescens are reared from cuttings in plastic pots filled with an earth/turf/sand mixture (1:1:1). After they have grown roots, the plants are transplanted into 9 cm pots and watered as required. For further growth the plants are then kept in a greenhouse at a day temperature of 27° C. and a night temperature of 21° C. The average light exposure is 14 hours (6000 lux) and the humidity is 70%. The plants are cut back to a height of about 15 cm and sprayed 7 days later with a spray mixture of the test compound (corresponding to a rate of application of 1 and 3 kg/a.i./ha respectively). Four weeks affer application the growth of the plants is compared with that of untreated control plants which have been cut back. It is found that compounds of Tables 1 to 3 effect a marked growth inhibition of the cover plants.

| Compound | Rate of application a. i. kg/ha | Size of plants compared with controls (%) (controls = 100%) | |
|---|---|---|---|
| | | Centrosema | Psophocarpus |
| 1 | 3 | 10 | 10 |
| 18 | 3 | 10 | 10 |
| 19 | 3 | 40 | 80 |
| 21 | 1 | 10 | 10 |
| 38 | 3 | 10 | 10 |
| 39 | 1 | 10 | 30 |
| 61 | 3 | 60 | 20 |
| 86 | 1 | 60 | 50 |
| 134 | 3 | 90 | 70 |
| 136 | 3 | 40 | 40 |

EXAMPLE 17

Termination of growth of cotton plants

Cotton plants of the "Delta Pine" variety are sown in plastic containers in a 2:1 mixture of earth/sand and reared in a greenhouse at temperatures of 20°-26° C. After two months the plants have developed to the 6-leaf stage. At this time the plants are sprayed with an aqueous dispersion of a compound of the formula I until thoroughly wetted. The rate of application corresponds to 2 kg a.i./ha. Evaluation is made about 1 month after application. Compared with untreated control plants, the compounds of formula I effect a marked reduction of new growth.

| Compound | Rate of application a. i. kg/ha | new growth compared with control plants (controls = 100%) |
|---|---|---|
| 19 | 2 | 17 |
| 21 | 2 | 17 |
| 43 | 2 | 14 |

What is claimed is:

1. 1-(4-Chlorophenoxy)-2-tert-butyl-2-hydroxy-3-methyl-3-(1H-1,2,4-triazol-1-yl)propane.

2. A composition for regulating plant growth which comprises an effective amount of a compound according to claim 1 and a carrier therefor.

3. The method of inhibiting plant growth which comprises applying to the plant or to the environs of its growth an effective amount of a compound according to claim 1.

4. 1-(4-Fluorophenoxy)-2-tert-butyl-2-hydroxy-3-methyl-3-(1H-1,2,4-triazol-1-yl)propane.

5. A composition for regulating plant growth which comprises an effective amount of a compound according to claim 4 and a carrier therefor.

6. The method of inhibiting plant growth which comprises applying to the plant or to the environs of its growth an effective amount of the compound according to claim 4.

* * * * *